US012806103B2

(12) United States Patent
Turer et al.

(10) Patent No.: US 12,806,103 B2
(45) Date of Patent: Nov. 24, 2026

(54) INDIVIDUAL BIOCONTAINMENT UNIT TO REDUCE INFECTIOUS OR COMMUNICABLE DISEASE TRANSMISSION TO HEALTHCARE WORKERS, BYSTANDERS, AND PATIENTS

(71) Applicants: University of Pittsburgh— Of the Commonwealth System of Higher Education, Pittsburgh, PA (US); UPMC, Pittsburgh, PA (US); The United States of America as Represented by the Secretary of the Army, Adelphi, MD (US)

(72) Inventors: David Michael Turer, Pittsburgh, PA (US); Cameron Good, Joppa, MD (US); Benjamin Schilling, Pittsburgh, PA (US); Heng Ban, Wexford, PA (US); Jason S. Chang, Bridgeville, PA (US); J. Peter Rubin, Pittsburgh, PA (US); Lucas A. Dvoracek, Pittsburgh, PA (US)

(73) Assignees: University of Pittsburgh—Of the Commonwealth System of Higher Education, Pittsburgh, PA (US); UPMC, Pittsburgh, PA (US); The United States of America as Represented by the Secretary of the Army, Washington, DC (US)

( * ) Notice: Subject to any disclaimer, the term of this patent is extended or adjusted under 35 U.S.C. 154(b) by 1084 days.

(21) Appl. No.: 17/917,890

(22) PCT Filed: Apr. 6, 2021

(86) PCT No.: PCT/US2021/026004
§ 371 (c)(1),
(2) Date: Oct. 7, 2022

(87) PCT Pub. No.: WO2021/207233
PCT Pub. Date: Oct. 14, 2021

(65) Prior Publication Data

US 2023/0142819 A1 May 11, 2023

Related U.S. Application Data

(60) Provisional application No. 63/028,773, filed on May 22, 2020, provisional application No. 63/014,795, filed on Apr. 24, 2020, provisional application No. 63/006,446, filed on Apr. 7, 2020.

(51) Int. Cl.
*A61G 10/00* (2006.01)
*A61B 46/20* (2016.01)
*A61B 90/00* (2016.01)
*A61G 10/02* (2006.01)

(52) U.S. Cl.
CPC ............ *A61G 10/005* (2013.01); *A61B 46/20* (2016.02); *A61B 90/05* (2016.02); *A61G 10/023* (2013.01)

(58) Field of Classification Search
None
See application file for complete search history.

(56) References Cited

U.S. PATENT DOCUMENTS

| | | | | |
|---|---|---|---|---|
| 6,357,445 | B1 * | 3/2002 | Shaw | A61B 46/30 128/853 |
| 6,916,238 | B2 | 7/2005 | Korman | |

(Continued)

FOREIGN PATENT DOCUMENTS

| | | | | |
|---|---|---|---|---|
| JP | 2006314382 A | | 11/2006 | |
| WO | WO-2016134052 A1 | * | 8/2016 | A61M 1/784 |

*Primary Examiner* — Yi-Shan Yang
(74) *Attorney, Agent, or Firm* — The Webb Law Firm

(57) ABSTRACT

A biocontainment assembly for use with a patient suspected of having or diagnosed with a transmissible disease(s)
(Continued)

capable of respiratory, airborne, contact, or droplet transmission includes a housing configured to be positioned over and at least partially enclose a head, neck, and/or torso of the patient. A sidewall of the housing includes an open portion contiguous with an at least partially open bottom portion of the housing, sized to fit over at least a portion of the head, neck, and/or a torso of the patient. The housing also includes an airflow opening for evacuating fluid from an interior defined by the housing. The assembly also includes a drape configured to extend across the open portion of the sidewall having a first portion removably connected to the housing and an opposing second portion configured to be draped over the torso, abdomen, waist, and/or legs of the patient.

20 Claims, 8 Drawing Sheets

(56) References Cited

U.S. PATENT DOCUMENTS

| | | | | |
|---|---|---|---|---|
| 10,842,697 | B1 * | 11/2020 | Comunale | A61G 10/005 |
| 10,967,204 | B1 | 4/2021 | Adams et al. | |
| 2004/0255937 | A1 * | 12/2004 | Sun | A61G 10/00<br>128/201.25 |
| 2005/0085686 | A1 | 4/2005 | Yuen | |
| 2016/0136024 | A1 * | 5/2016 | Poenisch | A61G 7/0005<br>600/21 |
| 2022/0062664 | A1 * | 3/2022 | Yuen | B03C 3/08 |

* cited by examiner

INDIVIDUAL BIOCONTAINMENT UNIT TO REDUCE INFECTIOUS OR COMMUNICABLE DISEASE TRANSMISSION TO HEALTHCARE WORKERS, BYSTANDERS, AND PATIENTS

This application is the United States national phase of International Application No. PCT/US2021/026004 filed Apr. 6, 2021, and claims priority to the following United States Provisional Patent Applications: Application No. 63/006,446, filed Apr. 7, 2020; Application No. 63/014,795, filed Apr. 24, 2020; and Application No. 63/028,773, filed May 22, 2020, the disclosures of which are hereby incorporated by reference in their entirety.

BACKGROUND OF THE INVENTION

Field of the Invention

The present disclosure is generally directed to an individual biocontainment assembly for covering a head, neck, and/or torso of a patient and, in particular, to a biocontainment assembly for reducing transmission (e.g., bacterial, viral, or other infectious transmission) from the patient to healthcare workers, bystanders, and other patients for patients infected with or suspected of being infected with transmissible infectious agents, such as the severe acute respiratory syndrome coronavirus 2 (SARS-CoV-2), and/or patients suspected of having or diagnosed with, a transmissible disease(s) capable of respiratory, airborne, contact, or droplet transmission, such as COVID-19.

Description of Related Art

Protective equipment and enclosures that provide biocontainment isolation are needed to limit spread of transmissible diseases, such as COVID-19. Such protective equipment and enclosures are often used in emergency departments, intensive care units, operating rooms, emergency medical services, field hospitals, and, for example, in Naval ships (e.g., the U.S.S. Theodore Roosevelt). The need for biocontainment isolation is heightened during performance of aerosol generating procedures (AGPs), such as intubation and extubation procedures. In particular, healthcare workers who regularly perform AGPs on patients infected with transmissible diseases that are capable of respiratory, airborne, contact, or droplet transmission, such as COVID-19, are at high risk for virus transmission.

In order to alleviate risks of transmissible diseases, healthcare workers can wear personal protective equipment (PPE). PPE is defined by the Occupational Safety and Health Administration (OSHA) as specialized clothing or equipment worn by an employee for protection against infectious materials. For healthcare workers, PPE may include a combination of eye and respiratory protection, such as goggles, surgical masks, respirator masks (e.g., N95 or N99 masks), face shields, full or partial facepieces, and powered air-purified respirators, which are worn while performing AGP procedures for infected patients. PPE may also be worn more generally during procedures as a precaution against infectious or communicable transmission. However, the demand for specialized PPE may outstrip supply, as has occurred during the COVID-19 pandemic, prompting researchers and clinicians to design alternative protective devices.

In addition to using PPE, during the COVID-19 pandemic, healthcare systems have deployed passive protective enclosures for use during AGP procedures, such as orotracheal intubation. For example, rigid barrier enclosures (RBEs), better known as "intubation boxes", have been widely deployed for use while performing AGPs. Numerous RBEs were rapidly introduced early in the COVID-19 pandemic to protect against the spread of COVID-19 during orotracheal intubation. While these enclosures may provide some protection from heavier droplets (which typically fall to the ground within seconds), passive RBEs, such as intubation boxes, may not protect providers from aerosolized viruses.

SUMMARY OF THE INVENTION

According to an aspect of the disclosure, a biocontainment assembly for use with a patient suspected of having or diagnosed with a transmissible disease(s) capable of respiratory, airborne, contact, or droplet transmission includes a housing configured to be positioned over and at least partially enclose a head, neck, and/or torso of the patient. The housing includes a top portion, an at least partially open bottom portion configured to rest on a substantially planar surface, and at least one sidewall extending between the top portion and the bottom portion. The sidewall includes an open portion contiguous with the at least partially open bottom portion of the housing, sized to fit over at least a portion of the head, neck, and/or a torso of the patient. The housing also includes an airflow opening extending through the top portion and/or sidewall of the housing for evacuating fluid from an interior defined by the housing.

The assembly also includes at least one drape configured to extend across the open portion of the sidewall having a first portion removably connected to the top portion and/or sidewall of the housing, and an opposing second portion configured to be draped over the torso, abdomen, waist, and/or legs of the patient.

The assembly also includes at least one vacuum adapter connected to the housing. The vacuum adapter includes an inlet covering the airflow opening of the housing and an outlet configured to be connected to a fluid conduit to place the interior of the housing in fluid communication with a vacuum and/or filter system through the vacuum adapter and the fluid conduit.

According to another aspect of the disclosure, a system for containment of fluid from a patient suspected of having or diagnosed with a transmissible disease(s) capable of respiratory, airborne, contact, or droplet transmission includes the biocontainment assembly and the fluid conduit connected to the vacuum adapter of the assembly. The system also includes a vacuum or negative pressure source connected to the interior of the housing through the vacuum adapter and fluid conduit.

According to another aspect of the disclosure, a system for containment of fluid from a patient suspected of having or diagnosed with a transmissible disease(s) capable of respiratory, airborne, contact, or droplet transmission includes the biocontainment assembly and fluid conduit connected to the vacuum adapter of the assembly. The system also includes at least one decontamination device connected to the fluid conduit. The decontamination device is configured for at least one of reduction, removal, redirection, inactivation, or disinfection of contaminated fluid passing from the interior of the housing of the biocontainment assembly through the fluid conduit.

According to another aspect of the disclosure, a biocontainment method for a patient suspected of having or diagnosed with a transmissible disease includes: positioning the biocontainment assembly around the head, neck, and/or torso of the patient; and applying negative pressure to the interior of the housing of the assembly through the fluid conduit and vacuum adapter, thereby evacuating fluid from the interior of the housing.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DESCRIPTION OF THE INVENTION

Figure 1A:
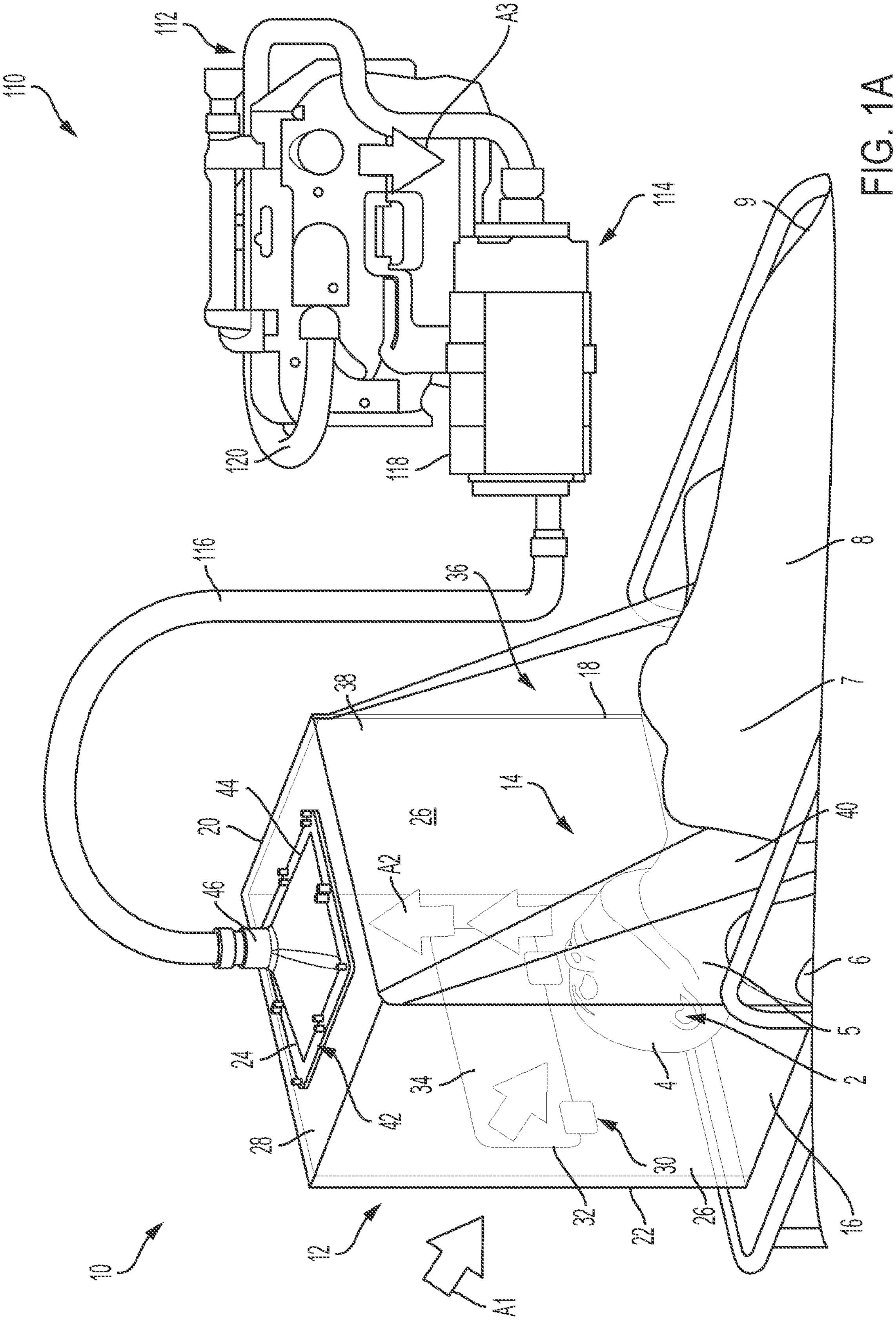
FIG. 1A is a schematic drawing of a biocontainment assembly and system including a filter and vacuum source.

As used herein, the singular form of “a”, “an”, and “the” include plural referents unless the context clearly states otherwise.

As used herein, the terms “right”, “left”, “top”, “bottom”, and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing, for example, dimensions, physical characteristics, and so forth used in the specification and claims are to be understood as being modified in all instances by the term “about.” Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any measured numerical value, however, may inherently contain certain errors resulting from the standard deviation found in their respective testing measurements.

Also, it should be understood that any numerical range recited herein is intended to include all sub-ranges subsumed therein. For example, a range of “1 to 10” is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms “comprising,” “comprise” or “comprised,” and variations thereof, are meant to be open ended.

As used herein, the term “patient” or “subject” refers to members of the animal kingdom including but not limited to human beings.

With reference to the figures, a biocontainment assembly 10 is provided comprising an enclosure or housing 12 for use with a patient 2 diagnosed with or suspected of having a transmissible disease that can be transmitted through respiratory secretions, such as COVID-19. As used herein, a “transmissible disease” may refer to an infectious, contagious, and/or communicable disease capable of being transmitted from one person to another person by, for example, respiratory, airborne, contact, or droplet transmission. The biocontainment assembly 10 can be for single-use (e.g., for use by a single patient during a single treatment event). Alternatively, components of the biocontainment assembly 10 or the entire assembly 10 may be sterilizable, so that components of the biocontainment assembly 10 or the entire assembly 10 can be reused by the same patient for multiple treatment events or for multiple patients.

In some examples, the assembly 10 is configured to be used as a component of a biocontainment system 110 and, in particular, is configured to be fluidly connected to a vacuum or negative pressure source 112 for active reduction, removal, redirection, inactivation, or disinfection of contaminated fluid from an interior 14 of the housing 12. As used herein, the term “fluid” refers generally to gasses and liquids including, for example, air which enters the interior 14 of the housing 12 through openings in the housing 12, airborne moisture, and respiratory secretions of the patient 2 including exhaled air and liquids (e.g., aerosolized water droplets, phlegm, saliva, etc.), as well as any other gasses and liquids that may be evacuated from the interior 14 of the housing 12 under negative pressure provided by the negative pressure source 112.

In some examples, the assemblies 10 and systems 110 disclosed herein have been designed and configured to address problems in protecting healthcare workers, bystanders, and other patients from transmissible diseases that have become apparent during the COVID-19 pandemic. First, the assemblies 10 and systems 110 disclosed herein may provide an alternative form of protection or at least supplement protections provided to healthcare workers by personnel protective equipment (PPE). During the COVID-19 pandemic, a lack of PPE placed healthcare workers at increased risk of acquiring and transmitting COVID-19 or a similarly transmissible disease, such as another coronavirus disease. The biocontainment assemblies 10 and systems 110 disclosed herein may provide suitable protections for healthcare workers even when PPE is not readily available and/or when PPE must be worn for extended periods of time due to limited supply.

Second, aerosolizing procedures (e.g., high flow nasal cannula (HFNC), CPAP, BiPAP, inhalers, nebulizers, etc.) often cannot be used for patients with a coronavirus infection, such as COVID-19, or a similarly transmissible disease, due to risks associated with aerosolized infectious secretions. Accordingly, treatment for patients with a coronavirus infection, such as COVID-19, or a similarly transmissible disease, often requires an increased reliance on ventilators, which, during the COVID-19 pandemic, were in critically low supply. However, healthcare workers who perform intubation and extubation of ventilator patients also are at increased risk of virus transmission, since such procedures require healthcare workers to be in close proximity to a patient's face and since there is a potential for the aerosolized virus to be inhaled. The biocontainment assemblies 10 disclosed herein are configured to provide protection for healthcare workers during such aerosolizing, intubation, and extubation procedures for patients with coronavirus infections, such as COVID-19, or a similarly transmissible disease, which may reduce risks to healthcare workers and increase treatment options for such patients.

Third, risks of viral transmission may be heightened during transport of patients from home to medical facilities or between medical facilities. In particular, EMS and in-hospital transportation of COVID-19 patients has been found to increase viral contamination. In order to address such risks, the biocontainment assemblies 10 and systems 110 disclosed herein may be portable and/or battery powered for use during transportation of COVID-19 patients.

Finally, social distancing and bed spacing requirements for patients diagnosed with or suspected of having COVID-19 or similarly transmissible diseases in place during the COVID-19 pandemic limited the number of patients per facility. Use of individual biocontainment units, such as the assemblies 10 and systems 110 disclosed herein, may allow patients to be placed more closely together since exhaled air and respiratory secretions from such patients are isolated and filtered to avoid contamination.

In some examples, the biocontainment assemblies 10 disclosed herein are configured to satisfy standards traditionally used for certifying laboratory hoods (e.g., Class I Biosafety Cabinets). In particular, the biocontainment assemblies 10 are configured to demonstrate one or more of the following performance characteristics: (1) contaminated air does not escape from within the housing 12 during normal operation; (2) contaminated air passes through filter(s) to remove pathogens (<0.01% penetrating through the filter); and (3) the negative pressure system should pull sufficient air into the housing 12 to prevent pathogens from escaping (≥75 feet per minute (fpm)). The biocontainment assemblies 10 have been found to satisfy these performance characteristics, as shown by the Examples and by the graphs in FIG. 4.

The biocontainment assemblies 10 provide for active evacuation and filtering of exhaled air and respiratory secretions from the patient 2. In order to provide such active filtering, the assemblies 10 are connected to the vacuum or negative pressure source 112 and filter 114 for removing contaminated air from the assembly housing 12. Through testing, it was determined that standard hospital wall suction may not provide adequate airflow to support this active air filtration. However, as described in further detail herein, using the biocontainment assembly 10 with custom or commercially available vacuum sources 112 with higher air flow rates and specialized filters was found to exceed filtration characteristics of a Class I Biological Safety Cabinet. In fact, it was determined that the biocontainment assemblies 10 can be capable of providing full containment of all aerosolized particulates.

In view of the test results and examples described herein, the present inventors have determined that by using the biocontainment assembly 10 with active air filtration, peri-intubation pre-oxygenation and bag valve mask ventilation procedures may be performed safely without increasing risk of contaminating providers. Also, the inventors have determined that the assemblies 10 can be used for awake patient isolation, meaning that the biocontainment assemblies 10 can be used for aerosolizing procedures (e.g., high flow nasal cannula, CPAP, BiPAP, and nebulizers). It is believed that being able to provide aerosolizing treatments will reduce reliance on ventilators for treatment of patients diagnosed with or suspected of having certain transmissible diseases. In contrast, the present inventors determined that passive physical barriers (e.g., RBEs or "intubation boxes") are inadequate for protecting healthcare workers, bystanders, and patients in an immediate vicinity of an aerosolized pathogen that is potentially infectious or communicable during aerosolizing procedures, such as with patients having COVID-19, or a similarly transmissible disease.

In some examples, individual containment systems, such as the biocontainment assemblies 10, may also be used in ships, planes, and helicopters, as well as field hospitals or other tightly quartered vicinities, to contain multiple infected patients and limit risk of exposure to others. In particular, the biocontainment assemblies 10 can be portable, and may be airlifted to any military, hospital, healthcare, containment, or quarantine facility around the world. It is believed that placing each patient into biocontainment isolation allows for a much greater patient density, while decreasing risk of viral transmission. In some instances, it has been estimated that using the biocontainment assemblies 10, patient density can be increased by 50% or more by reducing patient distancing from 6 feet down to 30 inches or less.

Biocontainment Assembly

Various examples of biocontainment assemblies 10 for use with a patient suspected of having or diagnosed with a transmissible disease(s) capable of respiratory, airborne, contact, or droplet transmission, such as COVID-19, are shown in FIGS. 1A-2C. The assemblies 10 comprise the housing 12 configured to be positioned over and at least partially enclose a head 4, neck 5, and/or shoulders 6 of the patient 2. For example, as described in further detail herein, the housing 12 can have an open bottom 16 and open side 18. The housing 12 is sized and configured to be placed around the patient's head 2, neck 5, and, in some cases, shoulders 6 and torso 7. The patient's neck 5, shoulders 6, and/or torso 7 can extend through the open portion 18 on the side of the housing 12.

The housing 12 further comprises a top portion 20 opposite the at least partially open bottom portion 16 and at least one sidewall 22 extending between the top portion 20 and the bottom portion 16. The bottom portion 16 can be configured to rest against a substantially planar or flat surface, such as a surface of a mattress, surgical or operating table, gurney, or similar patient support structure. The planar surface can be level or angled. For example, the surface may be angled to about 60° to support a patient in a reclined position. In some examples, the housing 12 comprises handles or straps connected, for example, to the sidewalls 22 or bottom portion 16 of the housing 12 for securing the bottom portion 16 of the housing 12 to the planar surface. The housing 12 may also include handles or straps on the top portion 20 of the housing 12 for picking up, repositioning, or transporting the housing 12. The sidewall 22 comprises or defines the open side portion 18, which, as shown in the figures, is contiguous with the at least partially open bottom portion 16 of the housing 12. As discussed previously, the open portions 16, 18 are sized to fit over the head 4, neck 5, and/or a torso 7 of the patient 2.

In some examples, interior surfaces of the top portion 20 and sidewalls 22 of the housing 12 are uncovered. In other examples, the biocontainment assembly 10 may comprise an interior disposable drape or sheet removably mounted to interior surface(s) of the top portion 20 and sidewalls 22 for covering walls of the housing 12 to prevent contamination of the interior surfaces of the housing 12. The sheet or drape could be replaced after each use to simplify cleaning of the housing 12 between uses.

The housing 12 can be any convenient size, which is large enough to be used for different sized patients, but not so large as to restrict access to the patient or to inhibit movement of bystanders and healthcare workers, such as a proceduralist 102 and assistant 104 (shown in FIG. 1B), around the patient 2. For example, the housing 12 may have a height ranging from about 10 inches to about 40 inches, a width ranging from about 10 inches to about 40 inches, and a depth ranging from about 8 inches to about 36 inches. In some examples, the housing 12 is a size and shape that can be nested or stacked. In this way, housings 12 can be nested or stacked together to conserve space during shipping so that housings 12 can be transported to medical facilities more easily.

The housing 12 further comprises an airflow opening 24 extending through the top portion 20 and/or sidewall 22 of the housing 12 for evacuating fluid from the interior 14 defined by the housing 12. For example, as shown in FIGS. 1A-2C, the airflow opening 24 is positioned in the center of the top portion 20 of the housing 12. In this way, air is drawn through the interior 14 of the housing 12 in a vertical direction, as shown by arrows A2 in FIGS. 1A and 1C, which is believed to promote good airflow through the housing 12. In other examples, the airflow opening 24 could be positioned in the sidewall 22 of the housing 12 or in other convenient locations. The airflow opening 24 is sized to promote evacuation of air and fluid from all portions of the interior 14 of housing 12. An airflow opening 24 that is too small may not effectively remove air and secretions for peripheral areas of the housing 12. For example, the airflow opening 24 can range in area from about 30 square inches to about 300 square inches.

In some examples, the housing 12 is a partially enclosed box formed from a rigid frame, such as a frame formed from aluminum, steel, rigid plastics, or other suitable rigid materials, and panels mounted to the frame, such as rigid flat panels used to form windows and protective enclosures. The panels can be connected together and to the frame by fasteners or adhesives. The top portion 20 of the box can be formed from a top panel. The box may further comprise opposing side panels 26 connected by a middle panel 28. As shown in FIG. 1A, the middle panel 28 is opposite the open side portion 18 of the housing 12. In some examples, the housing 12 is transparent, or sufficiently transparent, or clear. Using the transparent or clear housing 12 allows for visualization of the patient's head 4 through the sidewall 22 and/or top portion 20 of the housing 12. Also, the inventors have determined that use of a housing 12 that is not transparent or clear can be disorienting for the patient. Accordingly, the transparent, sufficiently transparent, or clear housing 12 also allows for visualization by the patient through the sidewall 22 and/or top portion 20 of the housing 12. For example, the panels 26, 28 of the housing 12 can be formed from a transparent or substantially transparent rigid plastic, such as acrylic (plexiglass) or polycarbonate sheets. The polycarbonate sheets may comprise Makrolon® 2458 manufactured by Covestro AG, Leverkusen, Germany.

In some examples, the housing 12 further comprises an access port 30 positioned, for example, to allow healthcare workers to place their hands into the interior 14 of the housing 12 to treat the patient 2. The access port 30 can comprise an access opening 32 extending through the sidewall 22 of the housing 12 and a cover 34 removably secured to the access opening 32, which seals the access opening 32 when not in use. The cover 34 may be connected to the housing 12 by hinges or similar pivoting connectors. Alternatively, the cover 34 can be entirely removed from the housing 12 in order to open the access port 30. In some examples, a seal or gasket may be provided around the opening 32 or periphery of the cover 34 to enhance the seal between the cover 34 and opening 32.

Figure 1B:
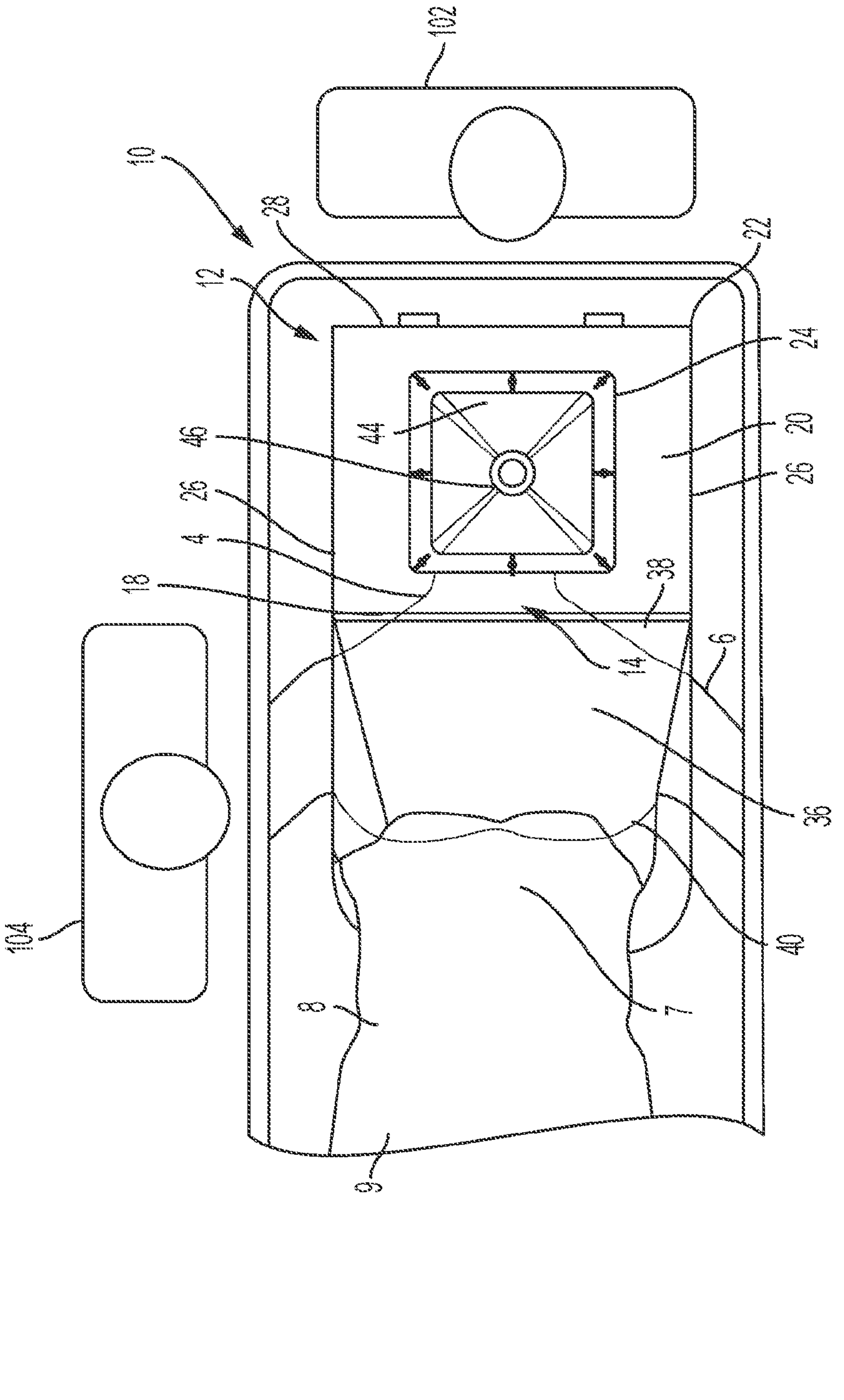
FIG. 1B is a schematic drawing of a top view of the biocontainment assembly of FIG. 1A.
Figure 1C:
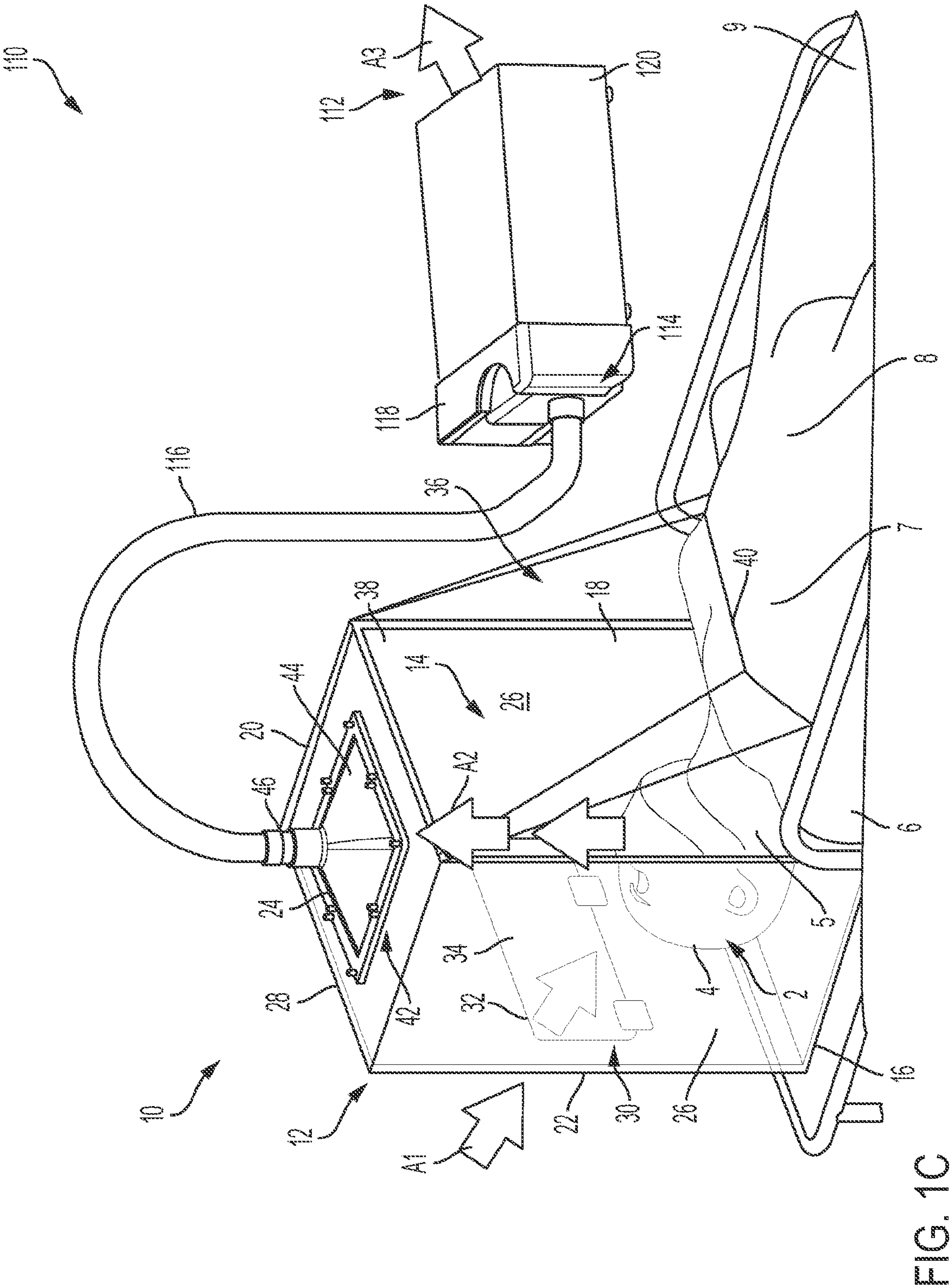
FIG. 1C is a schematic drawing of another example of a biocontainment assembly and system including an integrated filter and vacuum source.
Figure 3A:
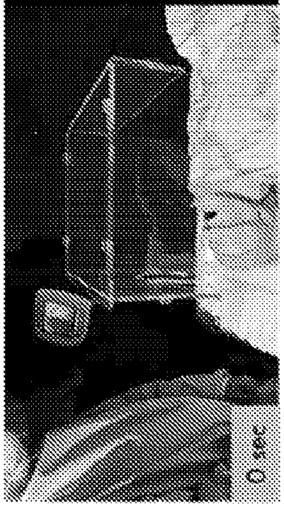
FIGS. 3A-3C are photographs showing a proceduralist performing an intubation procedure using a commercially available passive barrier enclosure, such as an intubation box.
Figure 3B:
Figure 3C:
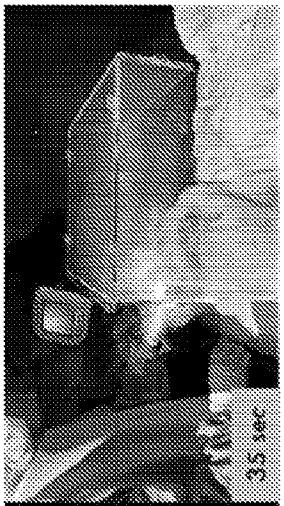
Figure 3D:
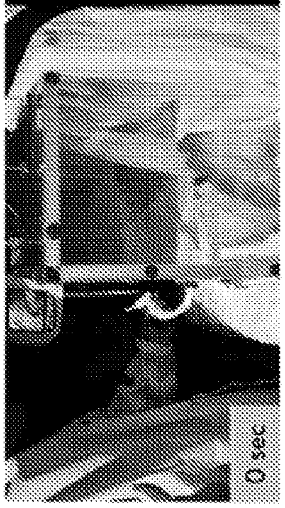
FIGS. 3D-3F are photographs showing a proceduralist performing an intubation procedure using a biocontainment assembly of the present disclosure.
Figure 3E:
Figure 3F:
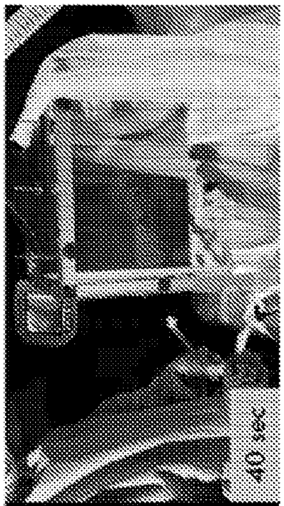

As shown in FIGS. 1A and 1C, the housing 12 comprises one access port 30 positioned on the middle panel 28 of the housing 12. The proceduralist 102 (shown in FIG. 1B) may place his or her hands through the opening 32 of this access port 30 to access the patient's mouth for performing aerosol generating procedures, such as intubation or extubation. The biocontainment assembly 10 may also be used to perform other procedures for patients diagnosed with or suspected of having transmissible diseases including, for example, endoscopy, bronchoscopy, surgical procedures, or dental procedures. Photographs of a proceduralist 102 performing an intubation procedure with the biocontainment assembly 10 are shown in FIGS. 3D-3F. For comparison, photographs of a proceduralist 102 performing an intubation procedure using a passive intubation box are shown in FIGS. 3A-3C. However, the arrangement of the access port 30 described previously and shown in FIGS. 3D-3F is not intended to limit the scope of the present disclosure and, in other examples, the housing 12 can comprise multiple access ports 30, such as access ports 30 located on each of the panels 26, 28 of the housing 12.

With continued reference to FIGS. 1A-2C, the assembly 10 further comprises a drape 36 configured to extend across the open side portion 18 of the housing 12. The drape 36 is configured to provide a seal over the patient 2, which can be lifted or adjusted for accessing the patient 2 and/or for permitting airflow into the interior 14 of the housing 12 to flush contaminated air through the housing 12. For example, the assistant 104 (shown in FIG. 1B) standing near the torso 7 of the patient 2 could access the torso 7 and/or chest region of the patient 2 by adjusting a position of the drape 36 to, for example, manipulate ventilator tubing, a bag valve mask, or other equipment.

The drape 36 can be a plastic sheet, such as a plastic sheet formed from low-density polyethylene or similar materials. The drape 36 can be transparent or partially transparent so that the proceduralist 102 and assistant 104 maintain good visualization of the patient 2. Also, including a transparent sheet or drape 36 may help prevent awake patients 2 from experiencing claustrophobia or other psychological phenomena when enclosed in the biocontainment assembly 10.

The drape 36 includes a first portion 38 or end configured to be connected to the sidewall 22 and top portion 20 of the housing 12. For example, the housing 12 and/or first portion 38 of the drape 36 may comprise fasteners, such as protrusions, detents, grommets, snaps, clips, and similar connectors, for securing the first portion 38 of the drape 36 to the housing 12. Alternatively or in addition, plastic sheeting of the drape 36 may include or be coated with an adhesive, such as a thin adhesive coating, placed symmetrically or asymmetrically on surfaces of the first portion 38 of the drape 36 for securing the drape 36 to surfaces of the housing 12, such as to exterior surfaces of the sidewall 22 and/or top portion 20 of the housing 12. Desirably, the connection between the drape 36 and the housing 12 is sealed to prevent contaminated fluid from escaping or leaking from the interior 14 of the housing 12 through gaps between the drape 36 and panels 26, 28 of the housing 12. The drape 36 also includes a second portion 40 or end configured to be draped over, for example, the torso 7, abdomen 8, and/or legs 9 of the patient 2. The drape 36 generally is not sealed around the patient 2 and, in some instances, may be open to permit air to flow into the interior 14 of the housing 12 through openings or spaces defined by the drape 36.

In some examples, the assembly 10 further comprises a support arm connected to and extending from the sidewall 22 of the housing 12 for supporting the drape 36. The support arm can be positioned to at least partially support the drape 36, such that portions of the drape 36 are supported or elevated above the torso 7 of the patient 2. For example, the assembly 10 may comprise two support arms extending from the sidewall 22, positioned on either side of the open portion 18. The drape 36 may be placed over the support arms so that the support arms hold the drape 36 above the patient's torso 7. The support arm(s) can be elongated members, such as a metal post, mounted to the housing 12 by fasteners. In some examples, the support arm comprises an axially extendable portion, which can be increased in length to increase an area of the drape 36 supported above the torso 7 of the patient 2. For example, the extendable portion may comprise a telescoping arrangement or portions formed from stretchable materials, which can be adjusted to increase or decrease a length of the support arm.

The biocontainment assembly 10 further comprises a vacuum adapter 42 connected to the housing 12 for proving a connection between the interior 14 of the housing 12 and external filter and vacuum systems. In some examples, the vacuum adapter 42 comprises an inlet 44 sized to cover the airflow opening 24 of the housing 12 and an outlet 46 configured to be connected to a fluid conduit 116 to place the interior 14 of the housing 12 in fluid communication with the filter and/or vacuum system through the vacuum adapter 42 and the fluid conduit 116. For example, the inlet 44 of the adapter 42 can be connected to the sidewall 22 of the housing 12 and sealed about the airflow opening 24 by conventional fasteners and seals, such as screws, clips, mounting brackets, gaskets, and similar structures, to prevent contaminated air and other fluids from escaping from the biocontainment assembly 10 through spaces or gaps between the vacuum adapter 42 and housing 12.

In some examples, the vacuum adapter 42 comprises a frustoconical or pyramid shaped body, in which a major dimension of the inlet 44 is wider than a major dimension of the outlet 46. In particular, the inlet 44 is wide enough to cover the airflow opening 24 of the housing 12. The outlet 46 is sized to be connected to the fluid conduit 116 and, accordingly, is appropriately dimensioned to receive or to be received within an end of the fluid conduit 116. Interior portions of the vacuum adapter 42 may be configured such that fluid flow through the adapter 42 (e.g., fluid flow from the inlet 44 to the outlet 46 of the adapter 42 under negative pressure from the negative pressure or vacuum source 112) has low turbulence or is non-turbulent. In some examples, as described in further detail in connection with FIGS. 2A-2C, the vacuum adapter 42 can contain a filter, such as a HEPA or ULPA filter, for filtering contaminated air and other fluids being evacuated from the interior 14 of the housing 12. Alternatively or additionally, as described herein, various inline filters can be connected in series with (e.g., to an end of) the fluid conduit 116 opposite from the vacuum adapter 42.

In order for components of the biocontainment assembly 10 to be easily available for use by different hospitals and other medical facilities, components of the assembly 10 are desirably easy to manufacture, purchase, obtain, and/or assemble, even during a pandemic. In order to facilitate widespread use, the vacuum adapter 42 can be formed by rapid prototyping or 3-D printing processes, as are known in the art. For example, CAD specifications for the vacuum adapter 42 may be made available to many hospitals and medical facilities, which may produce the vacuum adapter 42 from their own 3-D printing and rapid prototyping machines. As described herein, the hospitals and medical facilities may obtain or create other components of the assembly 10, such as the housing 12, drape 36, and vacuum or negative pressure source 112 using commercially available items that can be modified for use in the assemblies 10 disclosed herein. In other examples, components of the biocontainment assemblies 10, such as the housing 12 or drape 36, can be manufactured or customized specifically for use as a biocontainment assembly 10 to achieve heightened levels of viral containment and/or enhanced protective characteristics.

Biocontainment System

With continued reference to FIGS. 1A-2C, the biocontainment assemblies 10 disclosed herein can be integrated with a biocontainment system 110 for containment of fluids from a patient suspected of having or diagnosed with a transmissible disease(s) capable of respiratory, airborne, contact, or droplet transmission, such as a patient having a coronavirus infection, such as COVID-19. The system 110 can be used in hospitals and other medical facilities for isolation of individual patients and, in particular, for protecting caregivers from respiratory, airborne, contact, or droplet transmission of viral, bacterial, or otherwise potentially infectious or contagious agents during certain aerosol generating procedures.

The system 110 comprises the filter 114 for continuous filtration of contaminated air and other fluids evacuated from the interior 14 of the housing 12. As shown in FIGS. 1A-1C, the filter 114 is an inline filter device 118 connected to the fluid conduit 116 extending from the outlet 46 of the vacuum adapter 42. The inline filter device 118 can be separate from and connected to the vacuum or negative pressure source 112 by a second fluid conduit, as shown in FIG. 1A. In other examples, the filter device 118 is integrated with the vacuum source 112, as shown in FIG. 1C. In some examples, the filter 114 can be a decontamination device, such as a decontamination device configured for reduction, removal, redirection, inactivation, or disinfection of contaminated fluid(s) passing through the fluid conduit 116. In some examples, the filter 114 is configured to be used for a single patient and then disposed of. Alternatively, the filter 114 can be used for multiple patients.

The filter 114 can be a high efficiency particulate air (HEPA) filter, such as a filter having an MERV 16+ rating. Advantageously, it is believed that the same HEPA filters can be used for weeks or longer without replacement, helping to conserve scarce resources. The filter 114 would not need to be replaced for different patients. In other examples, the inline filter device 118 comprises an ultra-low particulate air (ULPA) filter, which is configured to capture smaller particles than the HEPA filter, thereby reducing post-filter penetration of contagious particles.

The system 110 further comprises the vacuum or negative pressure source 112 connected to the fluid conduit 116 and downstream from the filter 114 for drawing contaminated air from the interior 14 of the housing 12 and through the filter 114. In some examples, the negative pressure is a wall suction, such as wall suction outlets available at many hospitals and other medical facilities. Such wall suction systems generally operate at flow rates of about 300 mmHg. While wall suction flow rates may vary across hospital settings, such variance is unlikely to differ enough to alter operating characteristics of the containment system.

In other examples, the vacuum or negative pressure source 112 is a commercially available mechanical vacuum device 120 for producing a vacuum or negative pressure, such as a vacuum, fan, blower, air pump, or smoke evacuator. Such devices 120 may be manufactured specifically for use in medical environments and/or for use with containment systems. In other examples, commercially available non-medical vacuum devices 120 can be used with the systems 110 described herein. For example, the negative pressure source 112 can be a vacuum-producing device, fan, and/or a blower adapted to draw fluid from the interior 14 of the housing 12 through the fluid conduit 116. In some examples, the vacuum device 120 is a commercially-available wet/dry vacuum attached to the outlet 46 of the vacuum adapter 42. The vacuum devices 120 can be configured to provide negative pressure at an average airflow velocity of from about 10 feet per minute to about 200 feet per minute. For example, the vacuum device 120 can be configured to provide at least 10, 20, 30, 40, 50, 60, 75, 100, 150, or 200 feet per minute average airflow velocity to a patient 2, as measured in the interior 14 of the housing 12 and/or at the access port opening 32 of the housing 12.

In some examples, one or more of the following vacuum devices 120 can be used with the biocontainment assemblies 10 of the present disclosure: a portable DeWalt wet/dry vacuum (DeWalt, Baltimore, MD) coupled to an inline ultra-low particulate air (ULPA) filter cartridge (Atrix International Inc, Burnsville, MN); a Buffalo Filter PlumeSafe Turbo smoke evacuator with integrated filter (Buffalo Filter LLC, Lancaster, NY); a Buffalo Filter ViroVac smoke evacuator with integrated filter (Buffalo Filter LLC, Lancaster, NY); or a Neptune Smoke Evacuator (Stryker Corporation, Kalamazoo, MI).

When used in hospital settings, the negative pressure or vacuum source 112, such as the vacuum device 120, can be plugged into and receive power from a standard wall outlet (e.g., a wall outlet for providing AC power at 120 volts or 240 volts). Alternatively, the vacuum device 120 could be connected to an electrical generator for providing AC power. In other examples, the vacuum device 120 can be battery-powered. A battery-powered embodiment of biocontainment assembly 10 and vacuum system 120 with sufficient active air filtration could offer improved safety for emergency medical services and hospital-based patient transport. For example, the biocontainment assemblies 10 and systems 110 of the present disclosure can be used to isolate a patient (e.g., a patient suspected of having or diagnosed with COVID-19) during patient transport in situations when social distancing (e.g., maintaining spacing of at least about 1 meter to 2 meters between the patient and other individuals) is not possible and when intubation/ventilation is unable to be performed. In other examples, the biocontainment assemblies 10 and systems 110 of the present disclosure can be used for isolation of the patient for short-term (e.g., prior to intubation/ventilation) or long-term (e.g., hours, to days, to weeks) airway management.

Method of Setting Up and Use

In order to set up and use the biocontainment assembly 10 and system 110 described herein, a user first positions the biocontainment assembly 10 over the patient 2. For example, the user may position the housing 12 over the head 4 of a patient 2, with the patient 2 in a reclined or supine position, such that the open bottom 16 of the housing 12 rests against a planar surface (e.g., a surface of a mattress, hospital bed, operating table, etc.) and the sidewall 22 of the housing 12 partially surrounds the head 4, neck 5, and/or torso 7 of the patient 2. In this position, the patient's neck 5, shoulders 6, and/or torso 7 pass through the open side portion 18 of the housing 12. Next, the drape 36 is connected to the housing 12. For example, a user may attach the first portion 38 or end of the drape 36 to the housing 12, such that the drape 36 at least partially covers the open portion 18 in the sidewall 22 of the housing 12. The user then positions the second portion 40 or end of the drape 36 over the torso 7, abdomen 8, waist, and/or legs 9 of the patient 2 to at least partially isolate the patient 2 from bystanders, healthcare workers (e.g., from, the proceduralist 102 and assistant 104 shown in FIG. 1B), and others in proximity to the infectious patient 2.

After the housing 12 and drape 36 are suitably positioned about the patient 2, the user may connect the vacuum adapter 42 to the housing 12, such that the inlet 44 of the vacuum adapter 42 covers the airflow opening 24 of the housing 12. For example, the vacuum adapter 42 can be connected to the housing 12 by mechanical fasteners, such as screws, clips, mechanical brackets, and similar connectors. The outlet 46 of the adapter 42 is then connected to a fluid conduit 116, which is connected and/or in fluid communication with the inline filter device 118, if present, and the vacuum or negative pressure source 112.

Once the components of the system 110 are assembled, biocontainment of the patient 2 can be performed by applying negative pressure to the interior 14 of the housing 12 of the biocontainment assembly 10 through the fluid conduit 116 and vacuum adapter 42, thereby evacuating fluid from the interior 14 of the housing 12. Specifically, when the vacuum or negative pressure source 112 is activated, environmental air from outside of the interior 14 of the housing 12 can be drawn into the interior 14 of the housing 12 through, for example, the opening 32 of the access port 30 when the access port 30 is uncovered, as shown by arrows A1 in FIGS. 1A and 1C. In the interior 14 of the housing 12, the environmental air mixes with contaminated air and respiratory secretions from the patient 2. The contaminated air is drawn from the interior 14 of the housing 12, under the vacuum or negative pressure from the negative pressure source 112, through the airflow opening 24, and vacuum adapter 42, and into the fluid conduit 116, as shown by arrows A2. The evacuated contaminated air is the drawn through the inline filter device 118. The filtered air can be released back into the environment by the vacuum or negative pressure source 112, as shown by arrows A3.

Biocontainment Assemblies Made from Commercially Available Parts

Figure 2A:
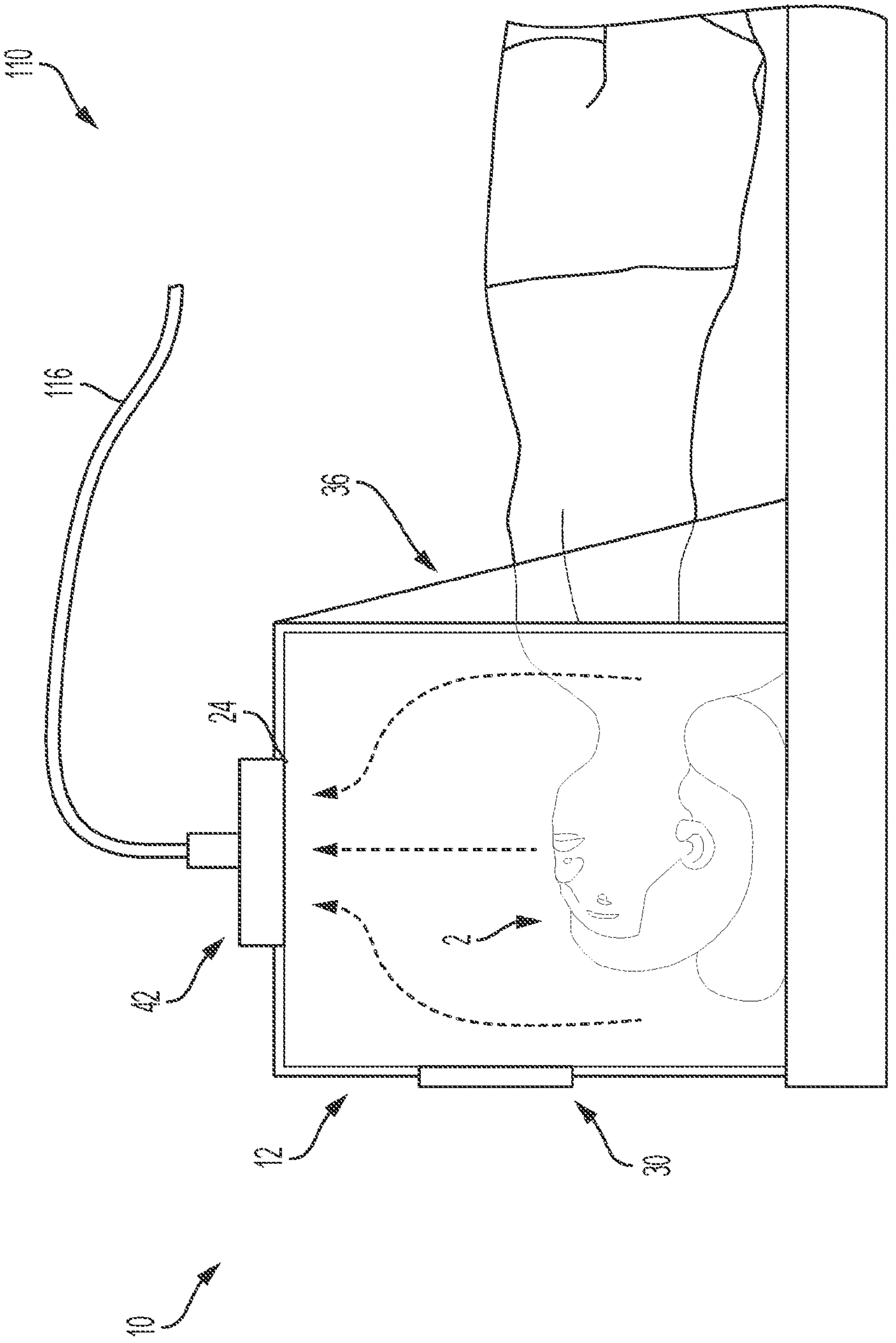
FIG. 2A is a schematic drawing of another example of a biocontainment assembly and system including a filter housed within a vacuum adapter of the assembly.
Figure 2B:
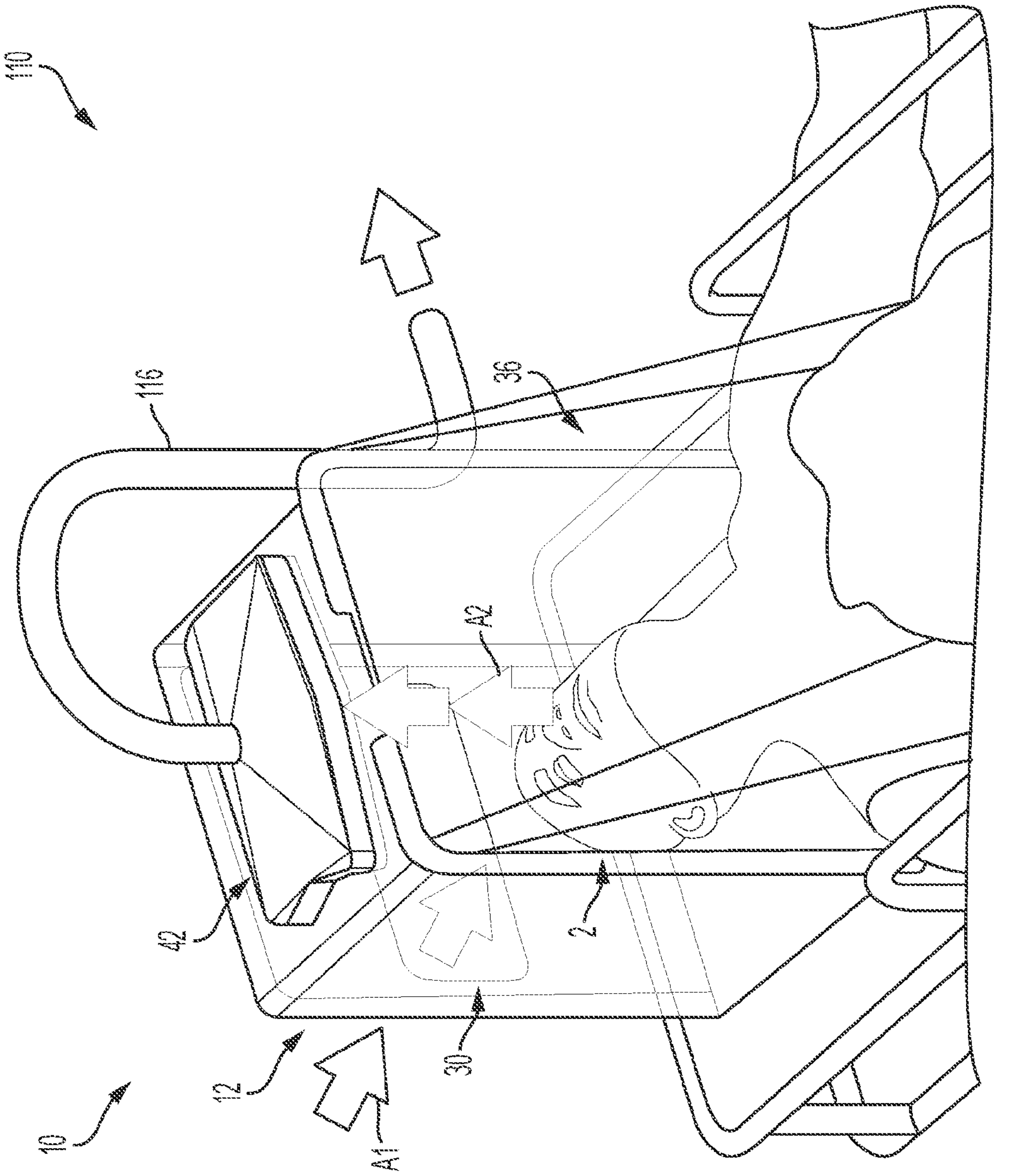
FIG. 2B is a schematic drawing of a perspective view of the biocontainment assembly of FIG. 2A.
Figure 2C:
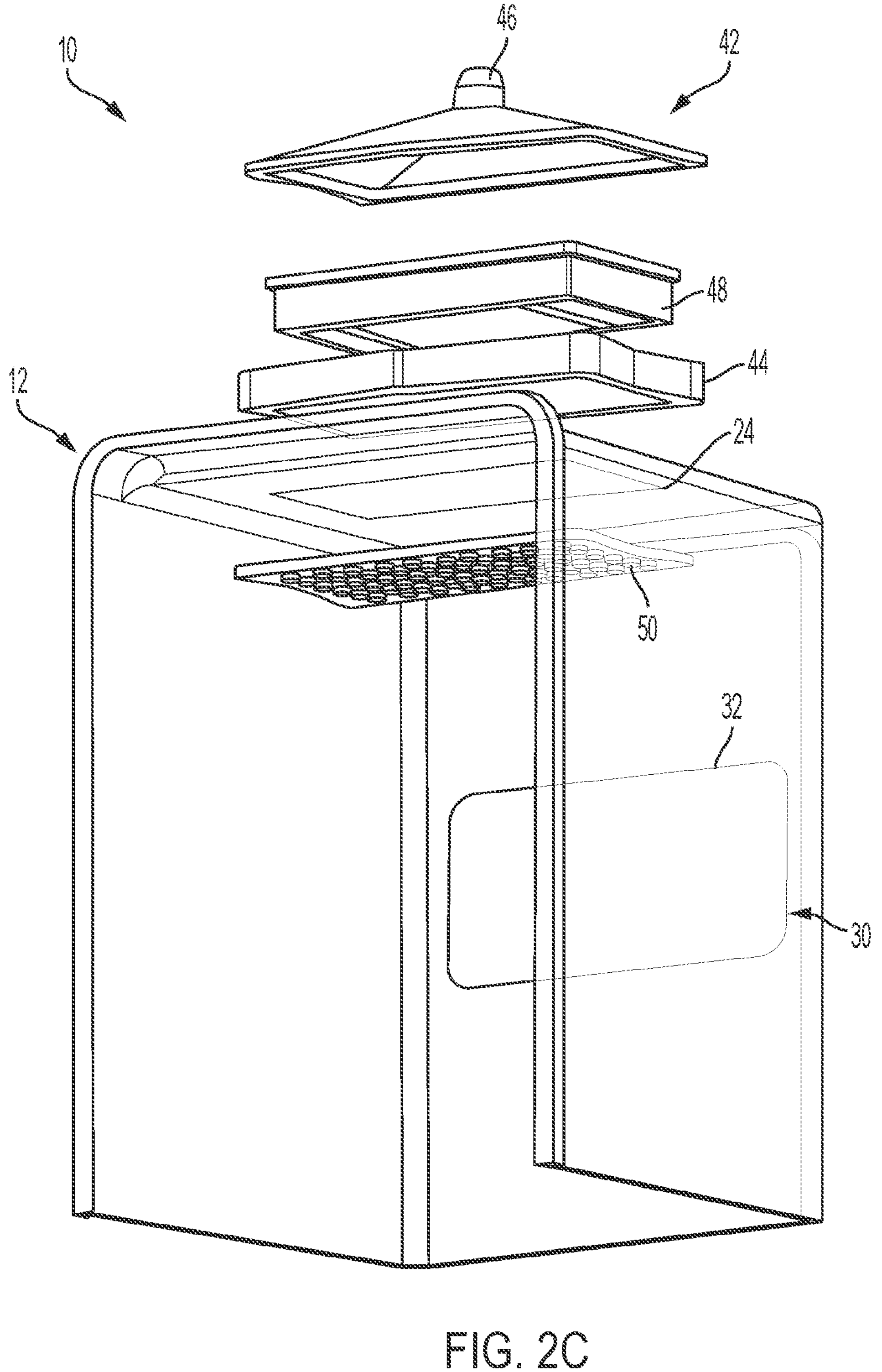
FIG. 2C is an exploded view of the vacuum adapter of the biocontainment assembly of FIG. 2A.

With specific reference to FIGS. 2A-2C, in some examples, the biocontainment assembly 10 of the present disclosure is intended to be constructed largely from commercially available components not typically used for ventilation and/or respiratory treatments for patients. For example, many of the components used in the biocontainment assembly 10 can be purchased from hardware stores, home and garden centers, and similar businesses. It is believed that use of biocontainment assemblies 10 that can be easily constructed from available parts not needed for other medical procedures and systems will help to alleviate shortages of medical, and particularly ventilator, components which have occurred during the COVID-19 pandemic.

For a biocontainment assembly 10 made from commercially available parts, the housing 12 can be formed from a modified storage bin, such as a STERILITE® plastic bin. Openings in the bottom 16 and sidewall 22 of the storage bin can be cut out, so that the bin can be positioned over the head 4, neck 5, and/or torso of the patient 2, as previously described. Also, the access port 30 and airflow opening 24 can be cut through sides of the storage bin so that the storage bin can be used as the housing 12, as described previously.

As shown in FIGS. 2A-2C, the vacuum adapter 42 can be modified to receive a conventional commercially available filter. For example, the vacuum adapter 42 can include a space or cavity between the inlet 44 and the outlet 46 sized to receive a commercially available air filter, such as a filter with a HEPA rating, UPLA rating, or a MERV 16+ rating. The assembly 10 shown in FIGS. 2A-2C can also include a grate 50, such as a metal mesh, covering the airflow opening 24 for preventing larger particles, solid matter, and other contaminates from entering the vacuum adapter 42 and contacting an enclosed filter 48. In some examples, the system 110 can also include an inline filter 114, similar to previously described inline filters 114, to supplement filtering by the enclosed filter 48.

The biocontainment system 110 shown in FIGS. 2A-2C includes and/or is configured to be connected to a vacuum source, such as the vacuum and/or negative pressure source 112 (shown in FIGS. 1A and 1C) fluidly connected to the interior 14 of the housing 12 (e.g., the storage bin) through the fluid conduit 116 and vacuum adapter 42. In use, contaminated air and respiratory secretions from the patient 2 are evacuated from the interior 14 of the housing 12 through the airflow opening 24. The contaminated air and secretions are filtered by the filter 48 enclosed within the vacuum adapter 42. The filtered air passes through the outlet 46 of the vacuum adapter 42 and through the fluid conduit 116 through the filter 114, if present, and towards the vacuum or negative pressure source 112, where the filtered air is expelled to the environment.

EXAMPLES

Enclosures including biocontainment assemblies of the present disclosure (i.e., the previously described biocontainment assembly 10 and vacuum system 110) and commercially available passive barrier enclosures (e.g., "intubation boxes") were evaluated using tests often used to certify Class I Biological Safety Cabinets. Results were compared between the biocontainment assemblies of the present disclosure, which are adapted to be used with active vacuum and filtration (referred to hereinafter as the "active RBE") and the passive barrier enclosures (referred to hereinafter as "the intubation box" or "the passive intubation box").

A primary objective of these Examples was to establish whether a passive intubation box could contain aerosols and satisfy industry safety requirements for Class I Biological Safety Cabinets, including smoke pattern analysis, aerosol leak testing, and air velocity testing. A secondary objection of these Examples was to compare aerosol concentrations as a surrogate for SARS-CoV-2 particles during intubation attempts between a passive intubation box and active RBE connected to different commercially available air filtration devices. Specifically, the following five configurations of active RBEs in connection with vacuum sources and/or filtration devices were used during testing of the enclosures: (1) hospital wall suction set to maximum pressure (>300 mmHg) without additional filtration; (2) a portable DeWalt wet/dry vacuum (DeWalt, Baltimore, MD) coupled to an inline ultra-low particulate air (ULPA) filter cartridge (Atrix International Inc, Burnsville, MN); (3) a Neptune Smoke Evacuator (Stryker Corporation, Kalamazoo, MI); (4) a Buffalo Filter PlumeSafe Turbo smoke evacuator with integrated filter (Buffalo Filter LLC, Lancaster, NY); and (5) a Buffalo Filter ViroVac smoke evacuator with integrated filter (Buffalo Filter LLC, Lancaster, NY)). The smoke evacuator featured adjustable fan speeds, and a wide range of settings. The enclosures were tested using various fan speeds and settings to determine system performance with a variety of flow rates.

Methods and Materials

A. Design and Setting

These Examples provide a simulation-based study evaluating RBE safety in a simulated hospital room. The Examples were performed using medical mannequins at the Winter Institute for Simulation, Education, and Research (Pittsburgh, PA). Air filtration testing was performed by Filtech Inc. (Homestead, PA) using a combination of International Organization for Standardization 14644-3 and Institute of Environmental Sciences and Technology test standards typically used for certifying Class I biosafety cabinets.

As a control, commercially-available passive intubation boxes (20 in×16 in×19 in) with two 5.75-in armholes for procedural access were obtained from VisionsAward, Celina, OH. Because commercially available passive intubation boxes lack the ability to incorporate active air filtration, a 16 in×13 in×21 in aluminum reinforced acrylic enclosure with a 3-D printed adaptor (7 in×7 in) was produced to connect the passive intubation boxes to filters and vacuum sources.

It is noted that the active RBE (e.g., the biocontainment assembly 10 of the present disclosure) included a rectangular window (12 in×5 in) for procedural access, which could be sealed when not in use. The caudal end of the active RBE was substantially sealed with a clear plastic tent or drape (similar to the drape 36 shown, for example, in FIGS. 1A-2B) placed around the mannequin.

B. Interventions

Aerosol containment during simulated intubation with both the passive intubation box and the active RBE was evaluated. In particular, simulated procedures were performed in which an attending emergency physician performed intubations by video laryngoscopy (GlideScope; Verathon Inc., Bothell, WA). Photographs of the simulated procedures are shown in FIGS. 3A-3F. During the simulated procedures, test aerosols were continually generated inside the passive intubation box and the active RBE, as described in the following experimental methods.

In order to perform the simulated procedures, the passive intubation box and the active RBE were placed over the mannequin's head and shoulders. Each simulation trial lasted 2.5 minutes, consisting of a 60-second preprocedural aerosol-generating period intended to simulate the peri-intubation period and allow accumulation of aerosol within the intubation box and active RBE Immediately after the preprocedural aerosol-generating period was a 90-second procedural period, during which the proceduralist repeatedly intubated and extubated the mannequin to simulate a failed airway scenario with multiple or prolonged intubation attempts. Aerosol generation continued during the simulated procedures. Three 2.5-minute trials were performed per test condition.

Negative-pressure isolation of an upright patient was also simulated using the active RBE. This configuration allowed for use of high-flow nasal cannula, continuous positive airway pressure, bilevel positive airway pressure, and other aerosol-generating procedures. The mannequin was positioned with the head of the bed elevated to 60 degrees and the active RBE was positioned over the mannequin's head and shoulders. A frame supported clear plastic sheet was positioned over the mannequin's lower body to create a tent or drape (similar to the drape 36 shown, for example, in FIGS. 1A-2B). The caudal end of the tent or drape was left open to allow room air entry and avoid potential claustrophobia. The procedural access window was sealed during isolation trials. Tests were performed with the following three commercially available smoke evacuators at their maximum setting: (1) Neptune Smoke Evacuator (Stryker Corporation, Kalamazoo, MI); (2) a Buffalo Filter PlumeSafe Turbo smoke evacuator with integrated filter (Buffalo Filter LLC, Lancaster, NY); and (3) a Buffalo Filter ViroVac smoke evacuator with integrated filter (Buffalo Filter LLC, Lancaster, NY). The DeWalt vacuum was not tested for use with simulated surgical procedures because the inventors believe that noise levels of the DeWalt vacuum would prohibit long-term use.

C. Methods of Measurement

To mirror Class I biosafety cabinet testing, the following three tests were performed: (i) qualitative smoke pattern analysis, (ii) quantitative aerosol leak testing, and (3) air velocity analysis.

i. Qualitative Smoke Pattern Analysis

Qualitative smoke pattern analysis is performed by observing neutrally buoyant glycol smoke within an enclosure (i.e. the passive RBE and the active RBE) to evaluate for escape of aerosol. Qualitative smoke pattern analysis is used as an indicator of airflow direction. Industry standards define test failure when smoke can be seen escaping the tested enclosure. In order to perform the smoke pattern analysis, glycol smoke was dispersed with a ° C. Breeze Fog Generator (Degree Controls Inc., Milford, NH) and released into the passive intubation box and active RBE enclosures directly above the mannequin's mouth. NSF-accredited technicians (for National Safety Foundation/American National Standards Institute Standard 49, Field Testing and Certification of Biological Safety Cabinets) performed and observed all visual smoke pattern analysis testing and classified each RBE as passing or failing. All technicians met and passed certification requirements for repeatable and reliable airflow smoke pattern tests as defined in National Safety Foundation/American National Standards Institute Standard 49.

ii. Quantitative Aerosol Leak Testing

Quantitative aerosol leak testing involves measuring particulate concentrations at enclosure openings and at filter exhaust ports to evaluate aerosol containment and filter performance, respectively. For this testing, a continuous flow of polydispersed polyalphaolefin (PAO) aerosol with an AG-E3 Laskin-nozzle Aerosol Generator (TEC Services Inc., New Oxford, PA) was generated and released directly above the mannequin's mouth at 56 μg/L. PAO aerosols generated in this manner contain particles from 0.1 μM to 10 μM, which corresponds to the size range of exhaled SARS-CoV-2 aerosolized droplets and is used as a laboratory surrogate of airborne pathogens. Aerosolized PAO particulate concentrations were measured inside and outside of each enclosure with a calibrated PH-5 photometer (TEC Services Inc.). To quantify PAO concentrations outside of the intubation box and active RBE enclosures, a photometer was used first to measure an average concentration of PAO (upstream) within each enclosure, which served as the 100% reference to quantify aerosol penetration outside of the enclosure (downstream). Downstream sample measurements were then acquired and reported as a percentage of the upstream concentration. Measurements were taken every 10 seconds, for a total of 10 measurements per trial, and repeated this 3 times, for a total of 30 PAO aerosol concentration measurements at each location for each configuration. Failure for this test was defined as when greater than 0.01% of PAO penetration was detected through the enclosure openings or the vacuum exhaust port.

iii. Air Velocity Analysis

In order to identify an air change rate for the enclosures, National Safety Foundation-accredited technicians (for National Safety Foundation/American National Standards Institute Standard 49) measured air velocity at 4 points evenly spaced across the procedural access window of the enclosure, using a 9565-A hotwire anemometer (TSI Incorporated, Shoreview, MN) to generate a mean value. Air changes per hour were extrapolated from the calculated mean value for air velocity and the procedural access window surface area. To meet Class I biosafety standards, a vacuum system must generate greater than 75 ft/min to prevent pathogens from escaping the hood.

For these Examples, performance of the passive intubation box was evaluated during simulated intubation, using qualitative smoke pattern analysis and quantitative aerosol leak testing. During the 90-second procedural period, PAO aerosol concentrations in front of the faces of the proceduralist (proceduralist 102 positioned as shown in FIG. 1B) and an assistant (assistance 104 positioned as shown in FIG. 1B) standing to the right of the mannequin were simultaneously measured. Passive intubation boxes do not actively filter air or generate airflow, so quantitative assessment of filter performance and air velocity testing could not be performed during these simulated procedures.

iv. Testing Methods for Active RBEs

The active RBE including features of the biocontainment assemblies 10 disclosed herein were similarly evaluated during simulated intubations, with the same above-described qualitative smoke pattern analysis and quantitative PAO aerosol concentration measurement techniques as those of the passive enclosure. Additionally, the active RBE enclosures underwent quantitative PAO filter leak testing at the vacuum exhaust port, as well as air velocity testing at the procedure access window. Measuring aerosol concentration at the exhaust port confirms that the test aerosol is not bypassing the filter and contaminating the environment.

Finally, during simulated negative pressure isolation, qualitative smoke pattern analysis, quantitative aerosol leak testing, and air velocity testing were performed for the active RBE outfitted with each of the three smoke evacuators. Air velocity at the open face of the plastic sheeting and quantitative aerosol concentrations at both the open end of the tent and 1.0 ft from the corner of the tent (at the position of the assistant 104 in FIG. 1B) were also measured.

D. Outcome Measures

The primary outcome studied by these Examples was to evaluate whether a passive intubation box contained aerosol as defined by passing the three safety tests necessary for Class I biosafety cabinet certification. Secondary outcomes of these Examples were the results of qualitative smoke pattern analysis, quantitative aerosol leak testing, and air velocity analysis on the active RBEs including features of the biocontainment assemblies 10 described herein.

E. Primary Data Analysis

Data was analyzed with GraphPad Prism software (version 8; GraphPad Software, San Diego, CA) and results were graphed with Excel (version 16.0.13029.20342; Microsoft, Redmond, WA). In these Examples, air velocity measurements are represented as mean with standard deviation (SD). PAO aerosol concentration measurements resulted in non-normal distributions and, therefore, are reported as median and interquartile range (IQR; 25th percentile, 75th percentile) to describe the populations from which the data were obtained. The obtained data is shown in the following Tables 1 and 3. Because it is not always possible to obtain an exact confidence interval (CI) for the median, GraphPad Prism finds and reports the closest confidence level possible (actual CI included later).

TABLE 1

Summary of results for each supine test configuration

| | Smoke | Filtration | Mean Face Velocity | Median Aerosol Concentration (%), N = 30, IQR (25th, 75th Percentile) | | Maximum Aerosol Concentration (%) | |
|---|---|---|---|---|---|---|---|
| Device Tested | Pattern Analysis | Efficiency (%) | (ft/min), N = 3 (SD) | Proceduralist Position | Assistant Position | Proceduralist Position | Assistant Position |
| Passive intubation box | Fail | N/A | N/A | 9.73 (3.14, 18.40) | 72.50 (8.58, 119.30) | 76 | 330 |
| Wall suction | Fail | N/A | 2 (0) | 11.30 (5.00, 39.43) | 0.19 (0.11, 0.29) | 148 | 2.18 |
| DeWalt shop vacuum + Atrix filter | Pass | 99.9988 | 69 (1) | 0.0011 (0.0006, 0.0024) | 0.0005 (0.0002, 0.0007) | 0.005 | 0.001 |
| Neptune 2 Ultra | Pass | 100.0000 | 66 (2) | 0.0012 (0.0001, 0.0046) | 0.0001 (0.0001, 0.0003) | 0.018 | 0.0021 |
| PlumeSafe Turbo | Pass | 99.9936 | 127 (1) | 0.0017 (0.0014, 0.0020) | 0.0016 (0.0013, 0.0017) | 0.007 | 0.002 |
| ViroVac | Pass | 99.9883 | 52 (2) | 0.0001 (0.0001, 0.0001) | 0.0014 (0.0011, 0.0016) | 0.005 | 0.002 |

TABLE 3

Summary of results for each test configuration when the head of the bed was elevated to 60 degrees (upright)

| | Smoke | Filtration | Mean Face Velocity | Median Aerosol Concentration (%), N = 30, IQR (25th, 75th Percentile) | | Maximum Aerosol Concentration (%) | |
|---|---|---|---|---|---|---|---|
| Device Tested | Pattern Analysis | Efficiency (%) | (ft/min), N = 3 (SD) | Open Position | Assistant Position | Open Position | Assistant Position |
| Neptune 2 Ultra | Pass | N/A | 44 (2) | Not tested | Not tested | N/A | N/A |
| PlumeSafe Turbo | Pass | N/A | 36 (4) | 0.0013 (0.0012, 0.0015) | 0.0014 (0.0012, 0.0015) | 0.002 | 0.002 |
| ViroVac | Pass | N/A | 14 (7) | 0.0015 (0.0012, 0.0019) | 0.0017 (0.0015, 0.0020) | 0.003 | 0.003 |

A clinically meaningful result was defined as a passive intubation box or active RBE test configuration's ability to maintain aerosol concentrations below the 0.01% industry threshold and not by effect size between different configurations. Protective efficacy of each configuration was confirmed by comparing the 99% CI (lower bound, upper bound) with the industry standard of 0.01%. If the CI does not contain the industry standard, then the median of that test configuration is significantly different. The 99% CIs for each test configuration are listed in Table 2 and Table 4 (actual CI 99.48%).

TABLE 2

Summary of CIs for each supine test configuration

| Device Tested | Median Aerosol Concentration (%), N = 30, 99% CI (Lower, Upper Bounds) Proceduralist Position | Assistant Position |
|---|---|---|
| Passive intubation Box | 9.73 (3.14, 17.70) | 72.50 (9.95, 118.00) |
| Wall suction | 11.30 (5.42, 39.20) | 0.19 (0.11, 0.28) |
| DeWalt shop vacuum + Atrix filter | 0.0011 (0.0006, 0.0021) | 0.0005 (0.0002, 0.0007) |
| Neptune 2 Ultra | 0.0012 (0.0001, 0.0045) | 0.0001 (0.0001, 0.0003) |
| PlumeSafe Turbo | 0.0017 (0.0014, 0.0020) | 0.0016 (0.0013, 0.0017) |
| ViroVac | 0.0001 (0.0001, 0.0001) | 0.0014 (0.0011, 0.0016) |

TABLE 4

Summary of CIs for each test configuration when the head of the bed was elevated to 60 degrees (upright).

| Device Tested | Median Aerosol Concentration (%), N = 30, 99% CI (Lower, Upper Bounds) Open Position | Assistant Position |
|---|---|---|
| Neptune 2 Ultra | Not tested | Not tested |
| PlumeSafe Turbo | 0.0013 (0.0012, 0.0015) | 0.0014 (0.0012, 0.0015) |
| ViroVac | 0.0015 (0.0012, 0.0019) | 0.0017 (0.0015, 0.0020) |

Measurements were taken at the caudal end of the tent or drape to simulate negative-pressure isolation. PAO aerosol concentrations are represented as median with 99% CI as a comparison against the industry standard safety limit of 0.01%.

Figure 4:
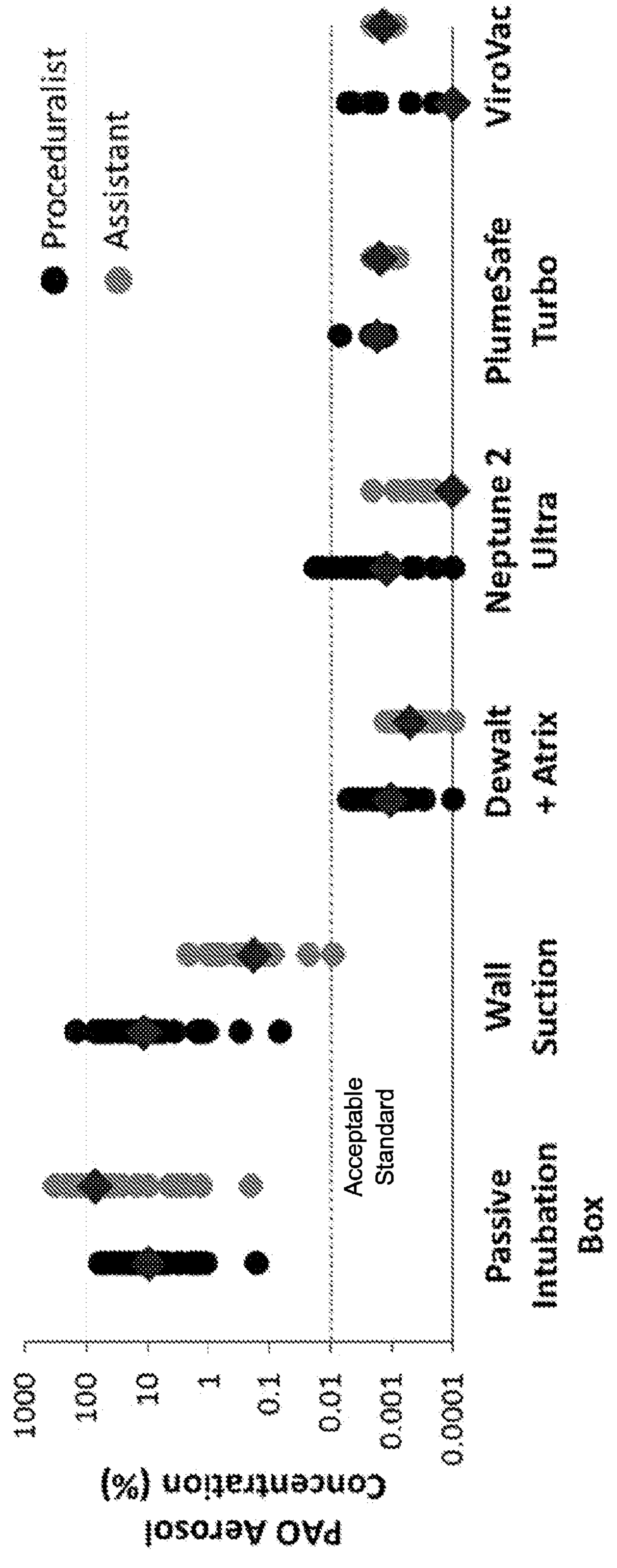
FIG. 4 is a graph showing results of aerosol concentration measurements obtained during testing of a commercially available passive intubation box and the biocontainment assemblies of the present disclosure.

FIG. 4 shows results of aerosol concentration measurements for the passive intubation box and for the active RBE with the above-described configurations of filters and vacuum sources. Relative concentration percentages of aerosolized PAO are plotted on a log scale for each test configuration. Measurements were taken simultaneously at the two locations (proceduralist, black circles; assistant, gray circles). Gray diamonds represent the median of all measurements for a given configuration. The horizontal dotted line represents the acceptable standard for aerosol concentration (<0.01%) outside the rigid plastic barrier enclosure.

Results

During simulated aerosol-generating procedures, the neutrally buoyant glycol smoke escaped from all openings in the passive enclosure, resulting in a failure of this test. Median quantitative measurements of PAO concentration as a percentage of concentration inside the passive rigid plastic barrier enclosure at the proceduralist location (9.73%; IQR 3.14%, 18.40%) and assistant location (72.50%; IQR 8.58%, 119.30%) were statistically significantly elevated above the industry standard acceptable level of 0.01%, resulting in a failure of this test. The maximum observed external PAO concentration was 330% at the assistant position, as shown in FIG. 4 and Tables 1 and 2, above.

A. Active RBE with Wall Suction

The active RBE connected to wall suction failed the qualitative smoke pattern analysis test. PAO concentration at the proceduralist's location (11.30%; IQR 5.00%, 39.43%) remained statistically significantly elevated above the industry standard acceptance of 0.01%. The maximum aerosol concentration measured at the proceduralist's location was 148%. Airflow velocity measurements at the procedure access window averaged 2 ft/min (SD 0 ft/min) (20 air changes per hour). Aerosol concentration at the assistant position (0.19%; IQR 0.11%, 0.29%) was reduced compared with the passive rigid plastic barrier enclosure (72.50%; IQR 8.58%, 119.30%) because of the addition of the clear plastic drape placed around the mannequin in active configurations. However, the PAO aerosol concentration still statistically significantly exceeded allowable safety levels of 0.01%, with a maximum measured concentration of 2.18%. See FIG. 4 and Tables 1 and 2, above.

B. Active RBE with DeWalt Vacuum

Higher airflow configurations for the active RBE were tested next. The first configuration tested was the portable DeWalt wet/dry vacuum and inline ultralow particulate air filter cartridge. This configuration passed the qualitative visual smoke test. PAO concentrations at both measurement locations outside the enclosure were statistically significantly below the industry safety threshold of 0.01% (proceduralist median=0.0011%, IQR 0.0006%, 0.0024%; assistant median=0.0005%, IQR 0.0002%, 0.0007%), thus meeting the acceptable standard for aerosol containment. See Table 1 and Table 2. This configuration produced an average air velocity of 69 ft/min (SD 1 ft/min) (682 air changes per hour).

C. Active RBE with Smoke Evacuators

The active RBE was also tested with the three surgical smoke evacuators run at multiple fan speeds. Each smoke evacuator passed qualitative smoke pattern analysis at all tested fan speed settings. When set to their maximum speed, all smoke evacuator systems statistically significantly maintained external PAO concentrations below the acceptable industry standard of 0.01% at each measurement location, as well as met Food and Drug Administration guidance for a 4-log reduction in aerosol concentration, thus meeting the acceptable standards of aerosol safety. See Table 1 and Table 2. Air velocities were recorded over the tested range of smoke evacuator fan speeds. At their maximum fan speeds, mean air velocity for the Neptune 2 Ultra, PlumeSafe Turbo, and ViroVac were 66 ft/min (SD 2 ft/min; 652 air changes per hour), 127 ft/min (SD 1 ft/min; 1,256 air changes per hour), and 52 ft/min (SD 2 ft/min; 514 air changes per hour), respectively.

Finally, testing was repeated during simulated negative pressure isolation with the head of the bed elevated. The active RBE using the three smoke evacuators passed qualitative smoke pattern analysis across all tested fan speeds. Quantitative aerosol concentration measurements at the tent or drape opening and assistant position remained statistically significantly lower than the 0.01% acceptable standard for each of the tested smoke evacuators at maximum fan speeds, passing this test. See Table 3 and Table 4. Fan speeds were varied and air velocities at the tent or drape opening were recorded. At their maximum settings, mean air velocities for the Neptune 2 Ultra, PlumeSafe Turbo, and ViroVac, and were 44 ft/min (SD 2 ft/min; 435 air changes per hour), 36 ft/min (SD 4 ft/min; 356 air changes per hour), and 14 ft/min (SD 7 ft/min; 138 air changes per hour), respectively. See Table 3.

Limitations

These Examples were performed in a medical simulation laboratory (Winter Institute for Simulation, Education, and Research) with a medical mannequin and industry-accepted aerosol test procedures as a surrogate to a patient with SARS-CoV-2 in a clinical setting. The inventors are unsure how these experimental results translate to a dynamic emergency department setting. Further, although a single commercially available passive intubation box was tested, the inventors believe that the above-reported results for the passive intubation box can be generalized to other commercially available enclosures, because most commercially available enclosures have common design features that were well represented in the model that was tested. Also, the biocontainment assemblies 10 of the present disclosure were designed to include a single, larger procedure window versus the two independent armholes in the passive RBE. Because the surface area of the opening was larger in the tested active RBE enclosures, it is reasonable to believe that the two armholes in the passive intubation box would be the same or more favorable in containing aerosol if appropriately redesigned with sufficient active air filtration.

The approach to safety testing and device performance in these Examples used well-described industry techniques that are translatable to other aerosol containment systems designed for reducing the spread of infectious pathogens. However, these experimental results apply only to the configurations tested and additional safety testing should be performed on new systems before implementation in a clinical setting. Additionally, wall suction flow rates may vary across hospital settings, but are unlikely to differ enough to alter the outcome of these experimental results.

The Examples disclosed herein did not measure the incremental benefit of using a barrier enclosure with active filtration compared to standard PPE. It is unknown whether any of these enclosure devices, when added to currently recommended airborne precautions for aerosol-generating procedures (e.g., negative-pressure room, N95 or powered air-purified respirators), reduce the incidence of infection among persons performing or assisting with intubation. However, using an active RBE would provide added protection in cases of PPE failure, including poor mask fittings, prolonged use or reuse of barriers and filters, or failed viral containment because of lack of negative-pressure ventilation in a room. It is further reasoned that use of active RBE would prevent environmental contamination during aerosol-generating procedures. Finally, despite performance of numerous video laryngoscopy-assisted intubations with the active RBE using active air filtration, a rigorous ergonomics study would be needed before the biocontainment assemblies 10 disclosed herein can be widely adopted.

Discussion

Although many enclosures provide some protection from heavier droplets (which typically fall to the ground within seconds), to the knowledge of the present inventors no data exist about whether passive intubation boxes protect healthcare workers from aerosolized viruses. As a result, these Examples used well-established standards traditionally used for certifying Class I biosafety cabinets. Smoke pattern analysis revealed aerosol passing through the access points of the passive intubation box and directly into the proceduralist's and assistant's faces. The passive intubation box also failed to contain aerosol during simulated intubations. The present inventors believe that such passive intubation boxes provide a false sense of security, which may pose a risk to healthcare workers.

During testing, it was observed that the neutrally buoyant glycol smoke was drawn out of the passive intubation box and upward toward the proceduralist's face. Although a ceiling-mounted hospital ventilation system was not explicitly tested, the present inventors hypothesize that use of such ventilation systems could exacerbate this phenomenon and increase spread of aerosol.

These Examples also show that adding standard hospital wall suction with either an intubation box or with the biocontainment assembly 10 of the present disclosure does not provide adequate airflow to support its use for active air filtration. Instead, by coupling the active RBE (i.e., the biocontainment assembly 10 of the present disclosure) to vacuum sources with higher airflow rates and specialized filters, a vacuum system (i.e., the vacuum system 110 of the present disclosure) can be produced with performance similar to that of a Class I biosafety cabinet. Further, the active RBE tested demonstrated full containment of all aerosolized particulates (>99.99% efficient) and meet Food and Drug Administration guidance of a 4-log aerosol reduction for filtered air systems. Thus, the present inventors believe that the active RBE disclosed herein afford a significant improvement in healthcare worker safety over conventional devices, such as a passive intubation box.

Adoption of active RBE, such as the biocontainment assemblies 10 of the present disclosure, with active air filtration (i.e., by the vacuum or negative pressure source 112 and filter 114 described hereinabove) may allow peri-intubation preoxygenation and bag-valve-mask ventilation without increasing risk of contaminating a healthcare worker. Given the protective efficacy during simulations of negative-pressure isolation, these active biocontainment assemblies will likely facilitate use of high-flow nasal cannula, continuous positive airway pressure, bilevel positive airway pressure, and nebulizers in COVID-19 patients, reducing reliance on ventilators.

In summary, these Examples are believed to show that simple physical barriers, such as passive intubation boxes, inadequately protect healthcare workers from aerosols. In contrast, active RBEs, which incorporate sufficient active air filtration, provide improved protection to healthcare workers during simulated intubations. Additionally, active RBE and filtration systems provide a means to safely isolate individual patients and may also protect healthcare workers during patient transport.

Non-limiting aspects or embodiments of the present invention will now be described in the following numbered clauses:

Clause 1: A biocontainment assembly for use with a patient suspected of having or diagnosed with transmissible disease(s) capable of respiratory, airborne, contact, or droplet transmission, the assembly comprising: a housing configured to be positioned over and at least partially enclose a head, neck, and/or torso of the patient, the housing comprising a top portion, an at least partially open bottom portion configured to rest on a substantially planar surface, at least one sidewall extending between the top portion and the bottom portion, the sidewall comprising an open portion contiguous with the at least partially open bottom portion of the housing, sized to fit over at least a portion of the head, neck, and/or a torso of the patient, and an airflow opening extending through the top portion and/or sidewall of the housing for evacuating fluid from an interior defined by the housing; at least one drape configured to extend across the open portion of the sidewall comprising a first portion removably connected to the top portion and/or sidewall of the housing, and an opposing second portion configured to be draped over the torso, abdomen, waist, and/or legs of the patient; and at least one vacuum adapter connected to the housing, the vacuum adapter comprising an inlet covering the airflow opening of the housing and an outlet configured to be connected to a fluid conduit to place the interior of the housing in fluid communication with a vacuum and/or filter system through the vacuum adapter and the fluid conduit.

Clause 2: The assembly of clause 1, wherein the transmissible disease capable of respiratory, airborne, contact, or droplet transmission is a coronavirus infection, such as COVID-19.

Clause 3: The assembly of clause 1 or clause 2, wherein the housing is transparent, or sufficiently transparent or clear to allow visualization of the patient's head through the sidewall and/or top portion of the housing and/or to allow visualization by the patient through the sidewall and/or top portion of the housing.

Clause 4: The assembly of any of clauses 1-3, wherein the housing comprises a partially enclosed box in which the top portion of the housing comprises a top panel and the at least one sidewall comprises opposing side panels connected by a middle panel, the middle panel being opposite the open portion of the at least one sidewall.

Clause 5: The assembly of clause 4, wherein the panels of the housing comprise rigid plastic, such as polycarbonate or acrylic.

Clause 6: The assembly of any of clauses 3-5, wherein the housing further comprises a rigid frame, and wherein the panels are mounted to the frame to form the partially enclosed box.

Clause 7: The assembly of any of clauses 1-6, wherein the housing further comprises at least one access port comprising an access opening extending through the at least one sidewall of the housing and a cover removably secured to the access opening which seals the access opening when not in use.

Clause 8: The assembly of clause 7, wherein the access port is positioned on a middle panel of the sidewall of the housing.

Clause 9: The assembly of any of clauses 1-8, wherein the at least one drape comprises a plastic sheet, such as a plastic sheet formed from low-density polyethylene.

Clause 10: The assembly of any of clauses 1-9, wherein the at least one drape is sealed to the sidewall and top portion of the housing, such that fluid does not escape the interior of the housing between the first portion of the drape and the housing.

Clause 11: The assembly of any of clauses 1-10, wherein the at least one drape is a sufficient length to extend from the housing over the torso of the patient.

Clause 12: The assembly of any of clauses 1-11, wherein the at least one drape is secured to the housing by at least one of clips, fasteners, or adhesives positioned around the open portion of the housing and/or on the first portion of the at least one drape.

Clause 13: The assembly of any of clauses 1-12, wherein the vacuum adapter comprises a frustoconical or pyramid shaped body in which a major dimension of the inlet is wider than a major dimension of the outlet.

Clause 14: The assembly of clause 13, wherein the vacuum adapter is shaped such that fluid flow through the vacuum adapter is substantially non-turbulent.

Clause 15: The assembly of any of clauses 1-14, further comprising a filter in an interior of the vacuum adapter, positioned such that fluid entering the adapter through the inlet passes through the filter, and exits the interior of the vacuum adapter through the outlet, the filter comprising a filter with a HEPA rating, a ULPA rating, or a MERV 16+ rating.

Clause 16: The assembly of any of clauses 1-15, further comprising a grate or protective guard connected to the housing covering the airflow opening, and located between the vacuum adapter and the interior of the housing.

Clause 17: The assembly of any of clauses 1-16, wherein the housing comprises an open commercial or commodity plastic storage bin, in which the airflow opening is cut through the storage bin, and the vacuum adapter is 3D-printed.

Clause 18: The assembly of any of clauses 1-17, further comprising an interior sheet removably mounted to an interior surfaces of the housing for covering walls of the housing to prevent contamination of the walls of the housing.

Clause 19: The assembly of any of clauses 1-18, further comprising at least one support arm connected to and extending from the sidewall of the housing, wherein the support arm is positioned to at least partially support the at least one drape over the patient, such that portions of the at least one drape are supported above the torso of the patient.

Clause 20: The assembly of clause 19, wherein the at least one support arm comprises an axially extendable portion, which can be increased in length to increase an area of the portions of the at least one drape supported above the torso of the patient.

Clause 21: The assembly of any of clauses 1-20, wherein the assembly is a single-use assembly configured to be disposed of following treatment of the patient.

Clause 22: The assembly of any of clauses 1-20, wherein the assembly is sterilizable, so that the assembly can be used for multiple patients.

Clause 23: A system for containment of fluid from a patient suspected of having or diagnosed with transmissible disease(s) capable of respiratory, airborne, contact, or droplet transmission, the system comprising: the assembly of any of clauses 1-22, the fluid conduit connected to the vacuum adapter of the assembly; and a vacuum or negative pressure source connected to the interior of the housing through the vacuum adapter and fluid conduit.

Clause 24: The system of clause 23, wherein the transmissible disease capable of respiratory, airborne, contact, or droplet transmission is a coronavirus infection, such as COVID-19.

Clause 25: The system of clause 23 or clause 24, wherein the vacuum or negative pressure source comprises at least one of a vacuum device, (e.g., a vacuum-producing device, such as a wet/dry vacuum), a fan, and/or a blower adapted to draw fluid from the interior of the housing through the fluid conduit (e.g., a commercially-available wet/dry vacuum, attached to the outlet of the vacuum adapter).

Clause 26: The system of clause 25, wherein the vacuum, fan, and/or blower is battery-powered, or can be powered by both a battery and an electrical source, such as an electrical outlet or a generator.

Clause 27: The system of any of clauses 23-26, wherein the vacuum or negative pressure source produces at least 10, 15, 20, 25, 30, 40, 50, 60, 75, 100, 150, or 200 feet per minute average airflow velocity to the patient, as measured in the interior of the housing.

Clause 28: The system of any of clauses 23-26, wherein the vacuum or negative pressure source produces from about 10 feet per minute to about 200 feet per minute airflow velocity, as measured in the interior of the housing and/or at an opening in the sidewall of the housing.

Clause 29: The system of any of clauses 23-28, further comprising at least one decontamination device connected to the fluid conduit between the vacuum or negative pressure source and the vacuum adapter, the decontamination device being configured for reduction, removal, redirection, inactivation, or disinfection of contaminated fluid(s) passing through the fluid conduit.

Clause 30: The system of any of clauses 23-28, further comprising an inline filter fluidly connected to the fluid conduit for filtering fluid evacuated from the interior of the housing due to negative pressure exerted by the vacuum or negative pressure source.

Clause 31: A system for containment of fluid from a patient suspected of having or diagnosed with a transmissible disease(s) capable of respiratory, airborne, contact, or droplet transmission, the system comprising: the assembly of any of clauses 1-22, the fluid conduit connected to the vacuum adapter of the assembly; and at least one decontamination device connected to the fluid conduit, the decontamination device being configured for at least one of reduction, removal, redirection, inactivation, or disinfection of contaminated fluid passing from the interior of the housing of the biocontainment assembly through the fluid conduit.

Clause 32: The system of clause 31, wherein the at least one decontamination device comprises an inline filter connected to the fluid conduit for filtering fluid from the interior of the housing.

Clause 33: The system of clause 31 or clause 32, further comprising a filter in an interior of the vacuum adapter, positioned such that fluid entering the vacuum adapter through the inlet passes through the filter, and exits the interior of the vacuum adapter through the outlet, the filter comprising a filter with a HEPA rating, a ULPA rating, or a MERV 16+ rating.

Clause 34: A biocontainment method for a patient suspected of having or diagnosed with a transmissible disease(s), the method comprising: positioning the biocontainment assembly of any of clauses 1-22 around the head, neck, and/or torso of the patient; and applying negative pressure to the interior of the housing of the assembly through the fluid conduit and vacuum adapter, thereby evacuating fluid from the interior of the housing.

Clause 35: The method of clause 34, wherein the patient is suspected of having, or is diagnosed with a coronavirus infection, such as COVID-19.

Clause 36: The method of clause 34 or clause 35, wherein positioning the assembly around the head, neck, and/or torso of the patient comprises: placing the housing of the biocontainment assembly about the head, neck, and/or torso of the patient, such that the patient's neck and/or torso passes through the open portion of the sidewall of the housing; connecting the first portion of the at least one drape to the housing and positioning the second portion of the at least one drape over the torso, abdomen, waist, and/or legs of the patient; securing the vacuum adapter over the airflow opening; and attaching the fluid conduit to the outlet of the vacuum adapter.

Clause 37: The method of clause 36, wherein placing the housing about the head, neck, and/or torso of the patient further comprises securing the bottom portion of the housing to the surface by handles or straps.

Clause 38: The method of clause 36 or clause 37, wherein the vacuum or negative pressure source produces from about 10 feet per minute to about 200 feet per minute airflow velocity, as measured in the interior of the housing and/or at an opening in the sidewall of the housing.

Clause 39: The method of clause 36 or clause 37, wherein the negative pressure produces at least 10, 15, 20, 25, 30, 40, 50, 60, 75, 100, 150, or 200 feet per minute average airflow velocity to the patient, as measured in the interior of the housing.

Clause 40: The method of any of clauses 34-39, further comprising accessing the patient through an opening of an access port in the sidewall of the housing, and performing an aerosol generating procedure for the patient through the access port.

Clause 41: The method of clause 40, wherein the aerosol generating procedure is intubation or extubation of an endotracheal tube through a mouth of the patient.

Clause 42: The method of any of clauses 34-39, further comprising accessing the patient through an opening of an access port in the sidewall of the housing, and performing one or more of the following procedures for the patient: endoscopy, bronchoscopy, surgical procedures, or dental procedures.

Clause 43: Use of the biocontainment assembly of any of clauses 1-22 for isolation of the patient, wherein the patient is suspected of having or is diagnosed with a coronavirus infection, such as COVID-19, for isolation of the patient as the patient is being transported when social distancing is not possible and intubation/ventilation cannot be performed.

Clause 44: Use of the biocontainment assembly of any of clauses 1-22 for isolation of the patient for short term or long term respiratory management.

The invention claimed is:

1. A biocontainment assembly for use with a patient suspected of having or diagnosed with a transmissible disease(s) capable of respiratory, airborne, contact, or droplet transmission, the assembly comprising:

a housing configured to be positioned over and at least partially enclose a head, neck, and/or torso of the patient, the housing comprising a top portion, and an at least partially open bottom portion configured to rest on a substantially planar surface, at least one sidewall extending between the top portion and the bottom portion, the sidewall comprising an open portion contiguous with the at least partially open bottom portion of the housing, sized to fit over at least a portion of the head, neck, and/or torso of the patient, and an airflow opening extending through the top portion of the housing for evacuating fluid from an interior defined by the housing;

at least one drape configured to extend across the open portion of the sidewall comprising a first portion removably connected to the top portion and/or sidewall of the housing, and an opposing second portion configured to be draped over the torso, abdomen, waist, and/or legs of the patient; and at least one vacuum adapter connected to the top portion of the housing, the vacuum adapter comprising an inlet having a first dimension and covering the airflow opening of the housing and an outlet having a second dimension and configured to be connected to a fluid conduit to place the interior of the housing in fluid communication with a vacuum and/or filter system through the vacuum adapter and the fluid conduit, wherein the first dimension is larger than the second dimension, and wherein an arrangement of the airflow opening and vacuum adapter interior is configured such that air within the interior moves vertically, thereby improving airflow within the interior.

2. The assembly of claim 1, wherein the transmissible disease capable of respiratory, airborne, contact, or droplet transmission is a coronavirus infection.

3. The assembly of claim 1, wherein the housing is transparent, or sufficiently transparent or clear, to allow visualization of the patient's head through the sidewall and/or top portion of the housing and/or to allow visualization by the patient through the sidewall and/or top portion of the housing, and wherein the housing comprises a partially enclosed box in which the top portion of the housing comprises a top panel and the at least one sidewall comprises opposing side panels connected by a middle panel, the middle panel being opposite the open portion of the at least one sidewall.

4. The assembly of claim 3, wherein the housing further comprises a rigid frame, and wherein the panels are mounted to the frame to form the partially enclosed box.

5. The assembly of claim 1, wherein the housing further comprises at least one access port comprising an access opening extending through the at least one sidewall of the housing and a cover removably secured to the access opening which seals the access opening when not in use.

6. The assembly of claim 1, wherein the at least one drape comprises a plastic sheet, and wherein the at least one drape is sealed to the sidewall and top portion of the housing, such that fluid does not escape the interior of the housing between the first portion of the drape and the housing.

7. The assembly of claim 1, wherein the at least one drape is a sufficient length to extend from the housing over the torso of the patient.

8. The assembly of claim 1, wherein the vacuum adapter comprises a frustoconical or pyramid shaped body, and wherein the vacuum adapter is shaped such that fluid flow through the vacuum adapter is substantially non-turbulent.

9. The assembly of claim 1, further comprising a filter in an interior of the vacuum adapter, positioned such that fluid entering the adapter through the inlet passes through the filter, and exits the interior of the vacuum adapter through the outlet, the filter comprising a filter with a HEPA rating, a ULPA rating, or a MERV 16+ rating.

10. The assembly of claim 1, further comprising a grate or protective guard connected to the housing covering the airflow opening, and located between the vacuum adapter and the interior of the housing.

11. The assembly of claim 1, wherein the housing comprises an open commercial or commodity plastic storage bin, in which the airflow opening is cut through the storage bin, and the vacuum adapter is 3D-printed.

12. The assembly of claim 1, further comprising an interior sheet removably mounted to an interior surface of the housing for covering walls of the housing to prevent contamination of the walls of the housing.

13. The assembly of claim 1, further comprising at least one support arm connected to and extending from the sidewall of the housing, wherein the support arm is positioned to at least partially support the at least one drape over the patient, such that portions of the at least one drape are supported above the torso of the patient, wherein the at least one support arm comprises an axially extendable portion, which can be increased in length to increase an area of the portions of the at least one drape supported above the torso of the patient.

14. A system for containment of fluid from a patient suspected of having or diagnosed with transmissible disease(s) capable of respiratory, airborne, contact, or droplet transmission, the system comprising:

the biocontainment assembly of claim 1, the fluid conduit connected to the vacuum adapter of the assembly; and a vacuum or negative pressure source connected to the interior of the housing through the vacuum adapter and fluid conduit.

15. The system of claim 14, wherein the vacuum or negative pressure source comprises at least one of a vacuum device, a fan, and/or a blower adapted to draw fluid from the interior of the housing through the fluid conduit.

16. The system of claim 15, wherein the vacuum, fan, and/or blower is battery-powered, or powered by both a battery and an electrical source.

17. The system of claim 14, further comprising an inline filter fluidly connected to the fluid conduit for filtering fluid evacuated from the interior of the housing due to negative pressure exerted by the vacuum or negative pressure source.

18. A system for containment of fluid from a patient suspected of having or diagnosed with a transmissible disease(s) capable of respiratory, airborne, contact, or droplet transmission, the system comprising:

the biocontainment assembly of claim 1, the fluid conduit connected to the vacuum adapter of the assembly; and at least one decontamination device connected to the fluid conduit, the decontamination device being configured for at least one of reduction, removal, redirection, inactivation, or disinfection of contaminated fluid passing from the interior of the housing of the biocontainment assembly through the fluid conduit.

19. A biocontainment method for a patient suspected of having or diagnosed with a transmissible disease(s), the method comprising:

positioning the biocontainment assembly of claim 1 around the head, neck, and/or torso of the patient; and applying negative pressure to the interior of the housing of the assembly through the fluid conduit and vacuum adapter, thereby evacuating fluid from the interior of the housing.

20. The method of claim 19, wherein positioning the assembly around the head, neck, and/or torso of the patient comprises:

placing the housing of the biocontainment assembly about the head, neck, and/or torso of the patient, such that the patient's neck and/or torso passes through the open portion of the sidewall of the housing;

connecting the first portion of the at least one drape to the housing and positioning the second portion of the at least one drape over the torso, abdomen, waist, and/or legs of the patient;

securing the vacuum adapter over the airflow opening; and attaching the fluid conduit to the outlet of the vacuum adapter.

* * * * *